United States Patent [19]

Knorpp et al.

[11] Patent Number: 5,072,360
[45] Date of Patent: Dec. 10, 1991

[54] CONTROL ARRANGEMENT FOR DENTAL FURNACES, ESPECIALLY MICROPROCESSOR-CONTROLLED PREHEATING FURNACES

[75] Inventors: Ernst Knorpp; Manfred Gantner, both of Leutkirch, Fed. Rep. of Germany

[73] Assignee: Kaltenbach & Voigt GmbH & Co., Fed. Rep. of Germany

[21] Appl. No.: 399,779

[22] Filed: Aug. 25, 1989

[30] Foreign Application Priority Data

Sep. 16, 1988 [DE] Fed. Rep. of Germany ....... 3831539

[51] Int. Cl.$^5$ .......................... A61C 13/20; F27B 17/02
[52] U.S. Cl. ...................................... 364/140; 364/143; 364/146; 110/192; 432/51
[58] Field of Search ............... 364/140, 141, 146, 143; 432/124, 51; 219/391, 494, 489, 501; 110/191, 192; 34/43, 45; 164/155, 457

[56] References Cited

U.S. PATENT DOCUMENTS 3,909,590 9/1975 Jensen et al. .......................... 219/390
4,114,024 9/1978 Donner ................................ 219/489
4,300,037 11/1981 Padden ................................ 219/497
4,796,688 1/1989 Gundlach et al. ................... 164/457

OTHER PUBLICATIONS

Labor Öfen Printed by the Company Mihn-Vogt, Dental-Gerätebau GmbH & Co. Kg, 11/1987.
DE-Z, "Dental-Labor", Issue 10, 1984, p. 1170.

Primary Examiner—Jerry Smith
Assistant Examiner—Paul P. Gordon
Attorney, Agent, or Firm—Scully, Scott, Murphy & Presser

[57] ABSTRACT

A control arrangement for dental furnaces, especially microprocessor-controlled preheating furnaces or ovens with controlled heating and with limited rate in the rise of the heating temperature.

The control arrangement for dental furnaces implements the temperature control or rise on one or more, preferably three program tiers or levels, with one or more temperature steps or phases being either unrestrictedly or controllably programmed, or implemented on one or more temperature steps in a controlled programming.

35 Claims, 24 Drawing Sheets

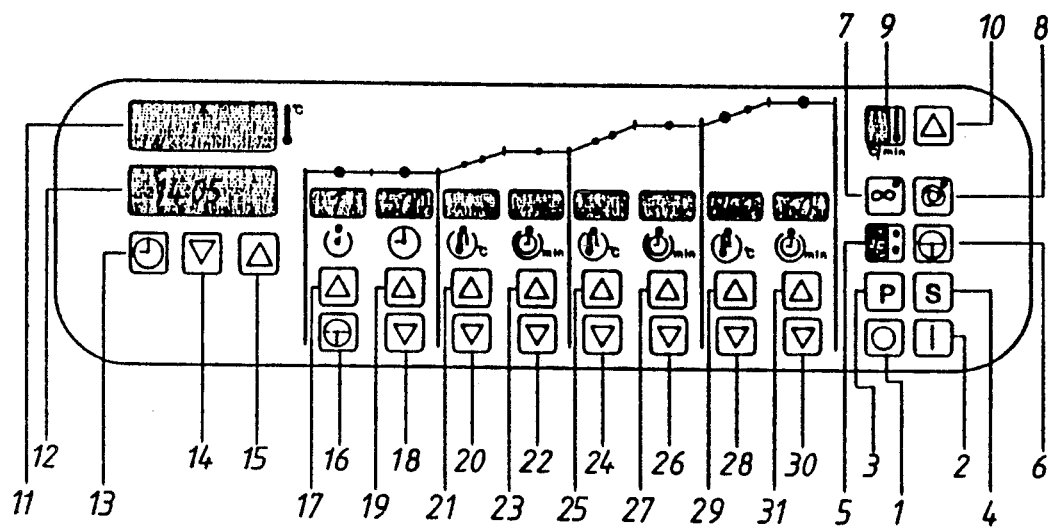
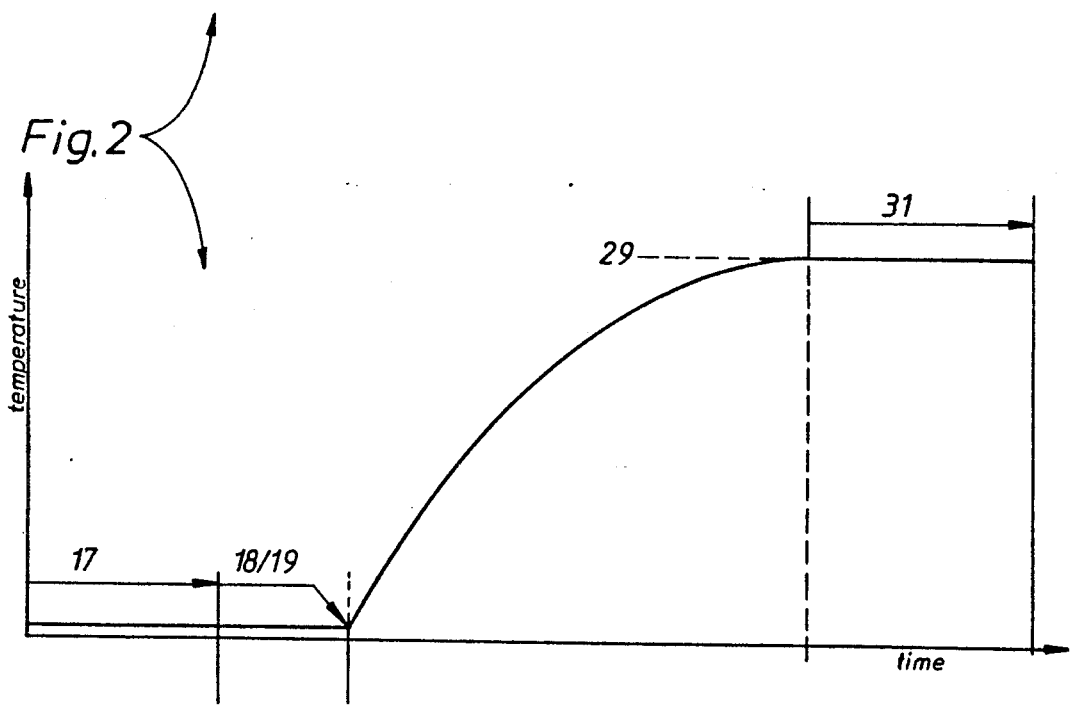
Fig. 2

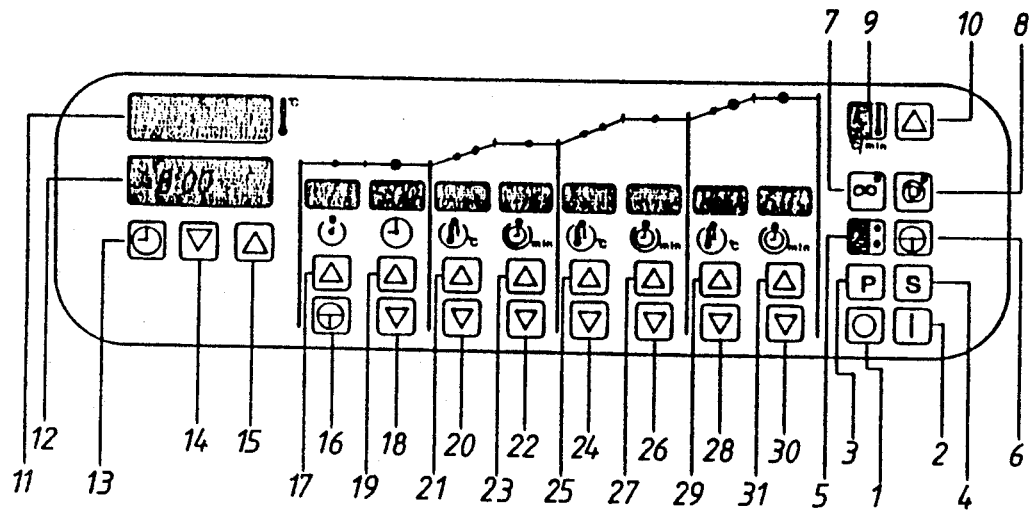
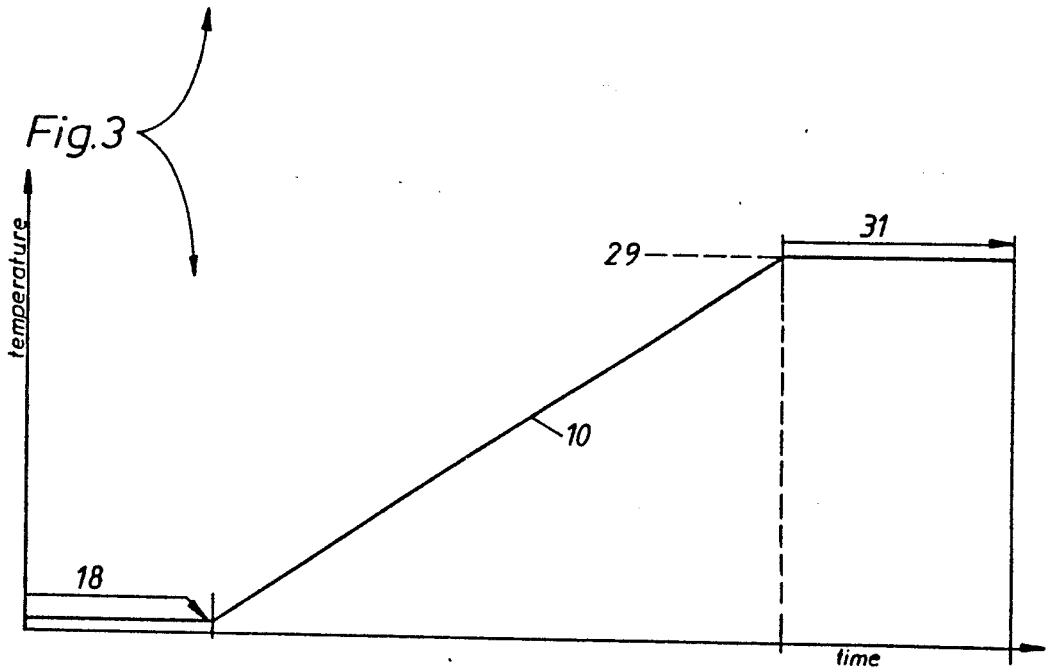
Fig. 3

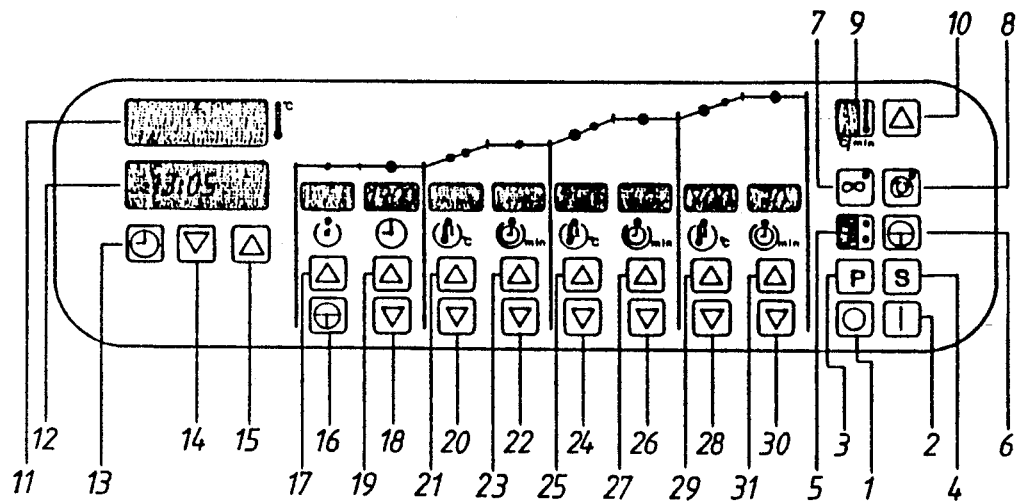
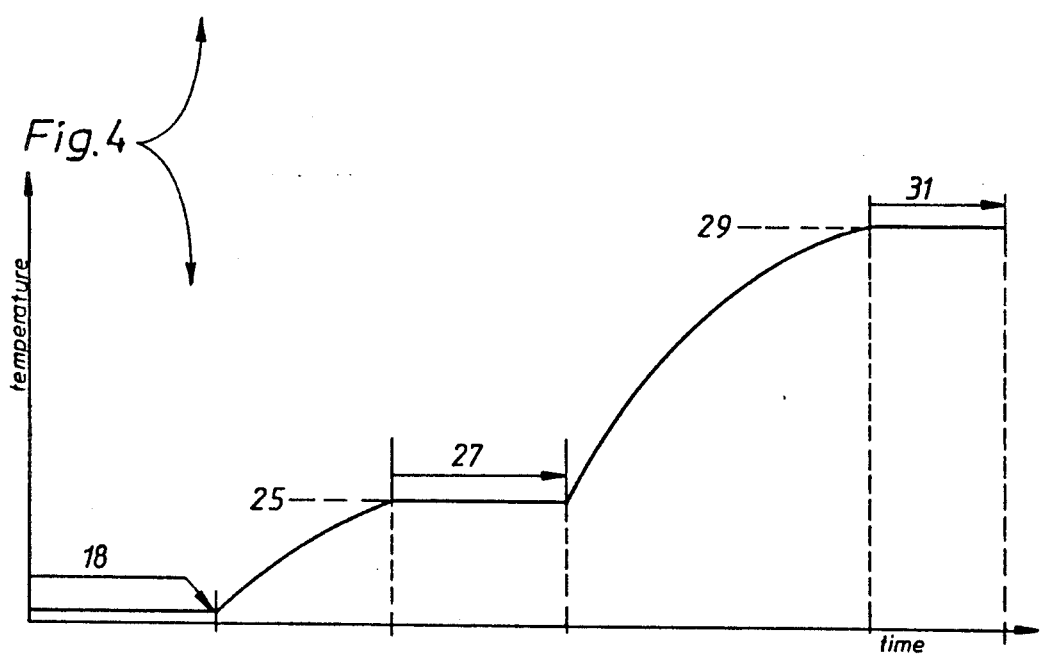
Fig. 4

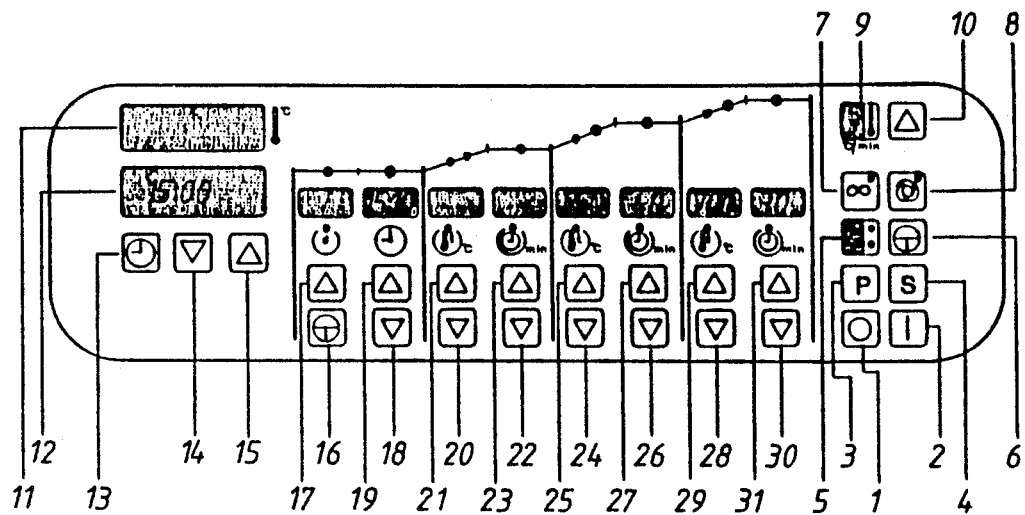
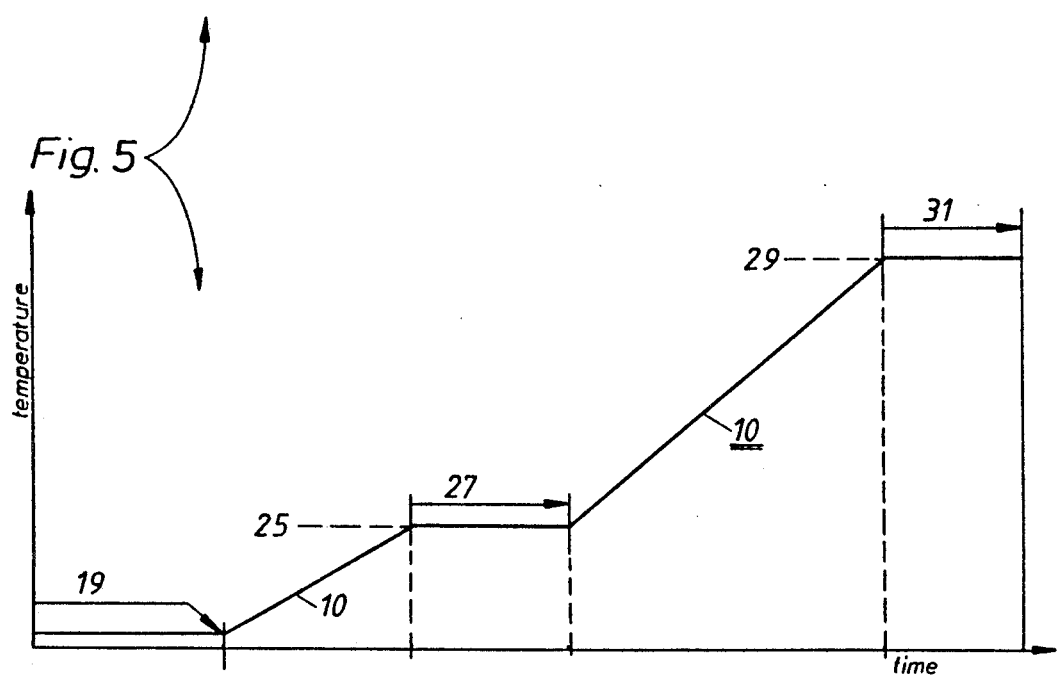
Fig. 5

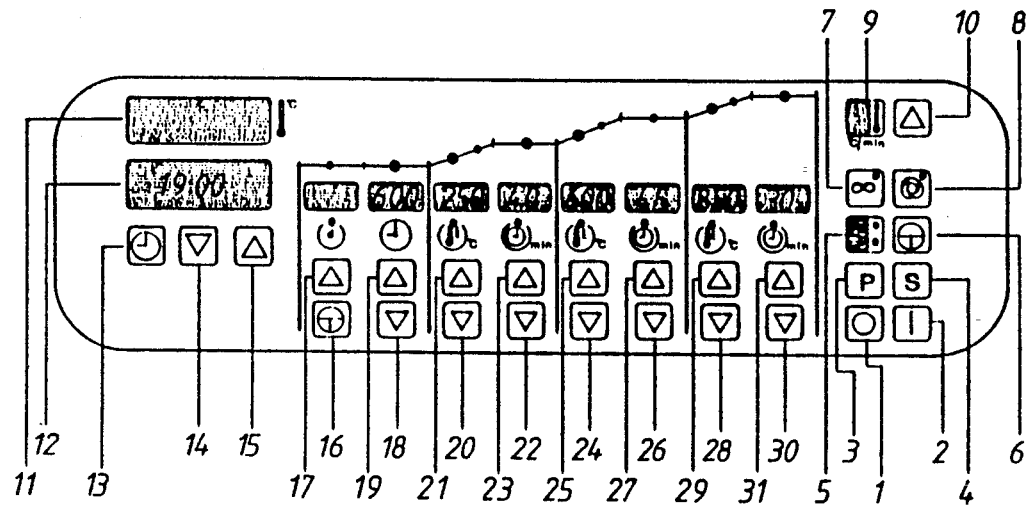
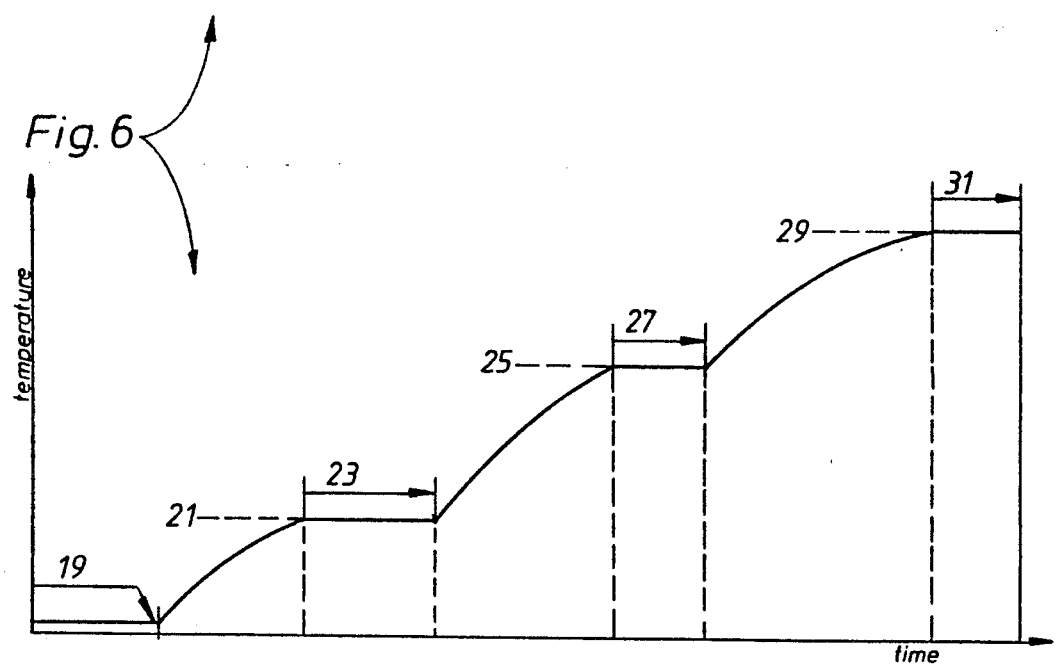
Fig. 6

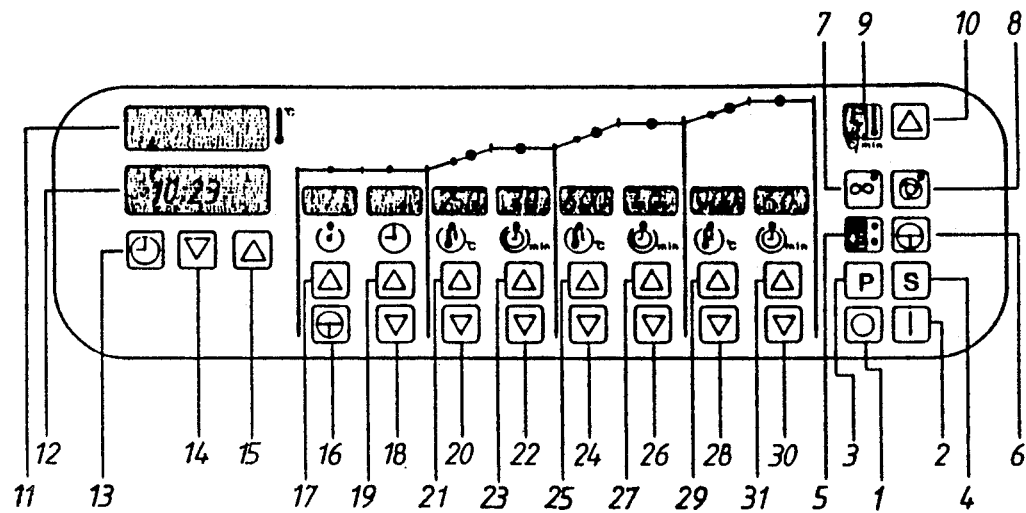
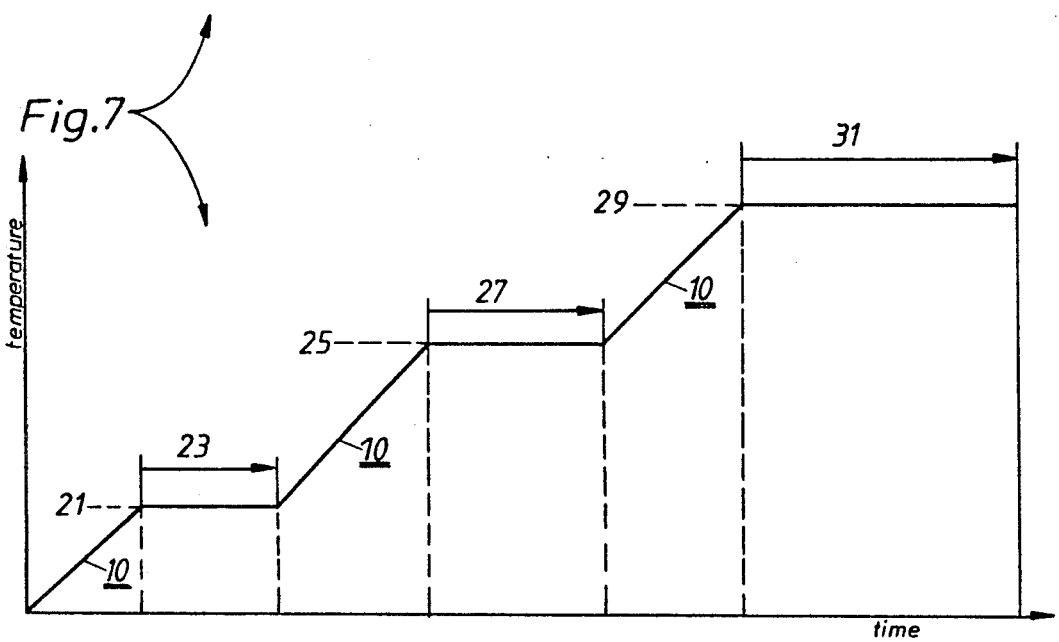
Fig. 7

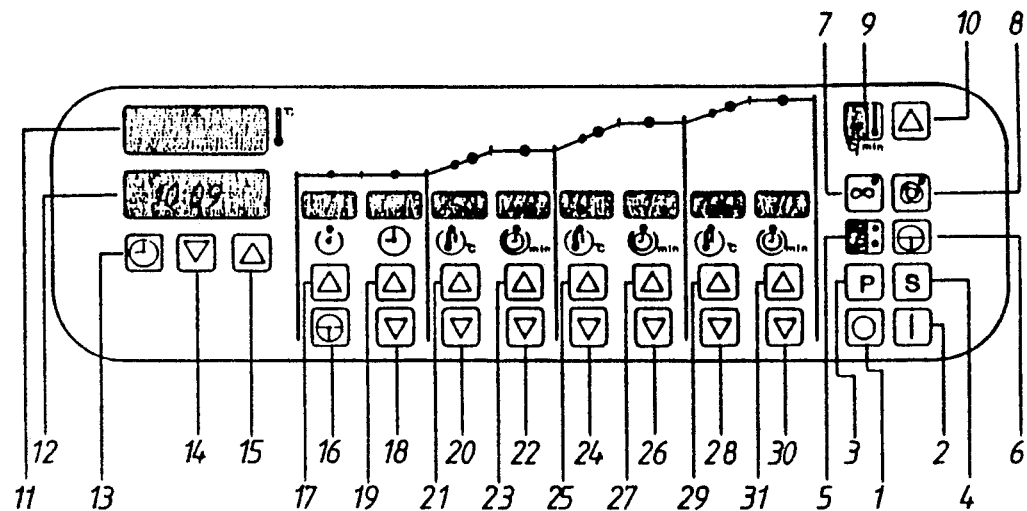
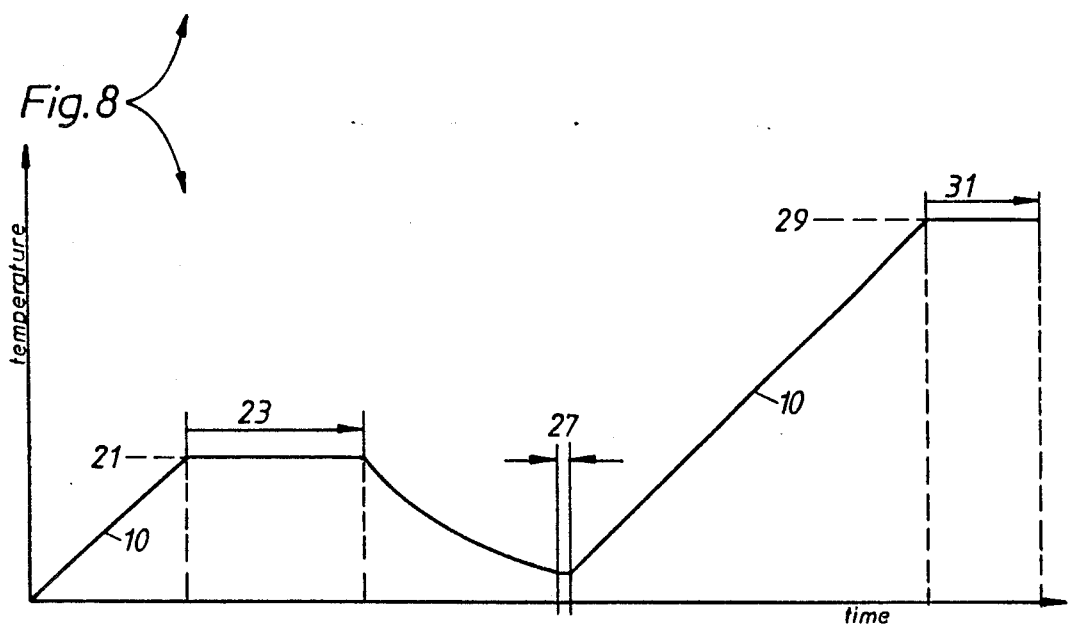
Fig.8

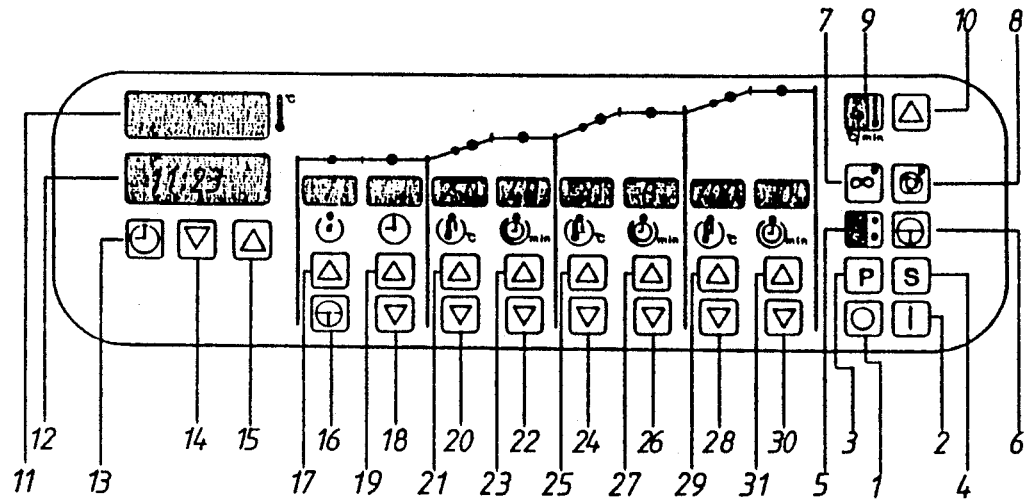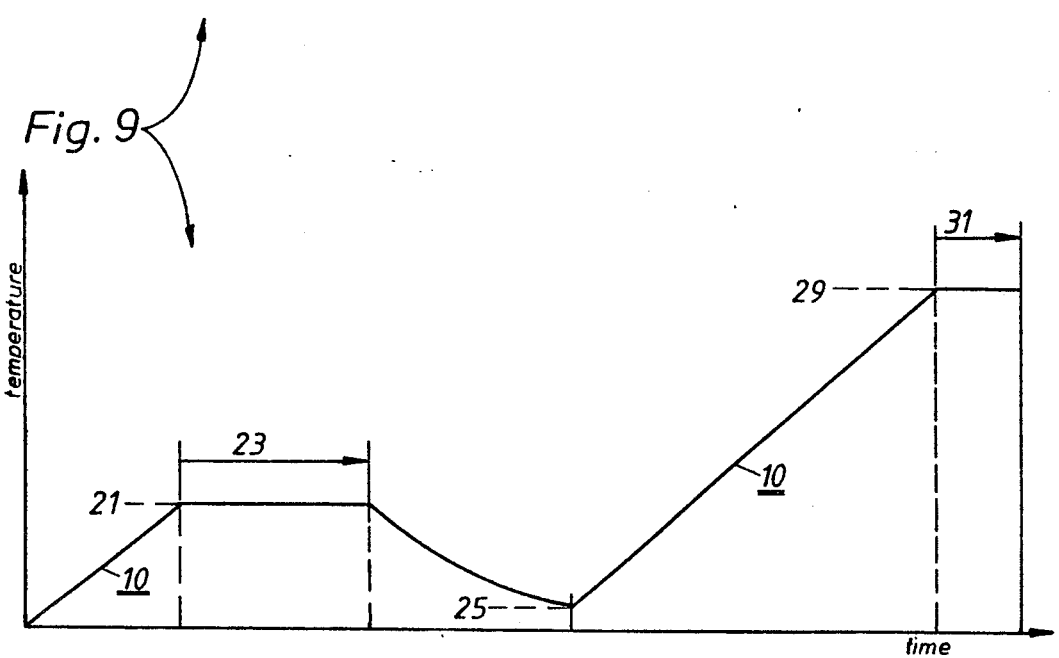
Fig. 9

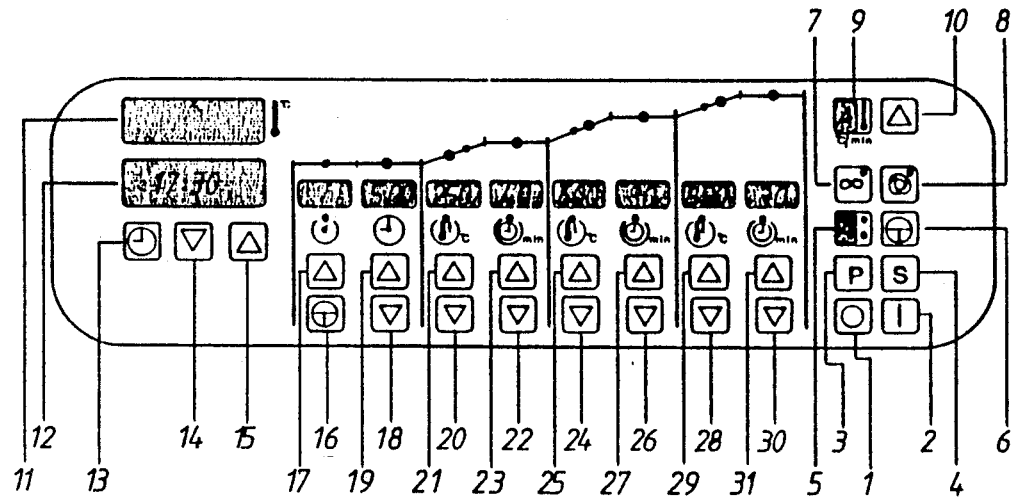
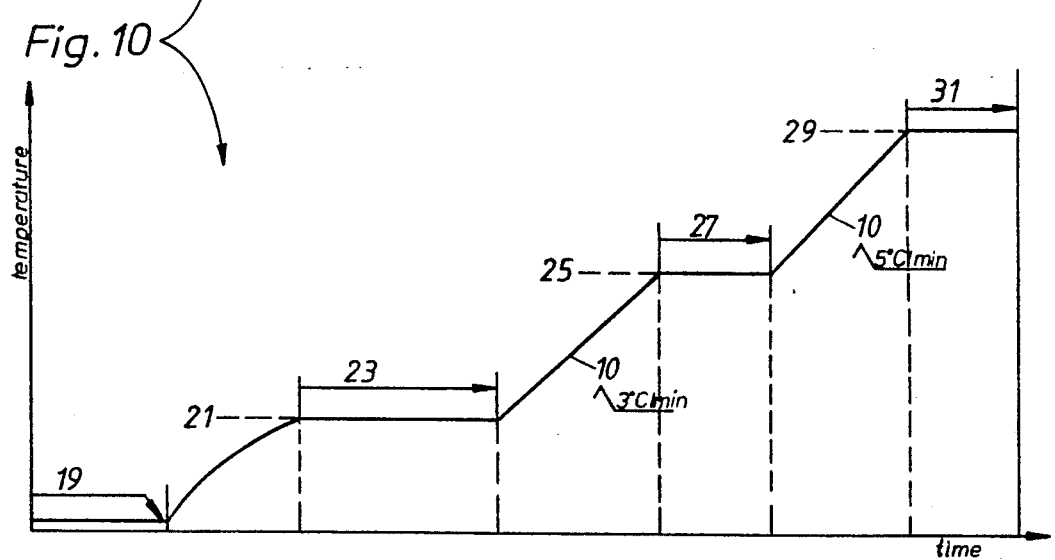
Fig. 10

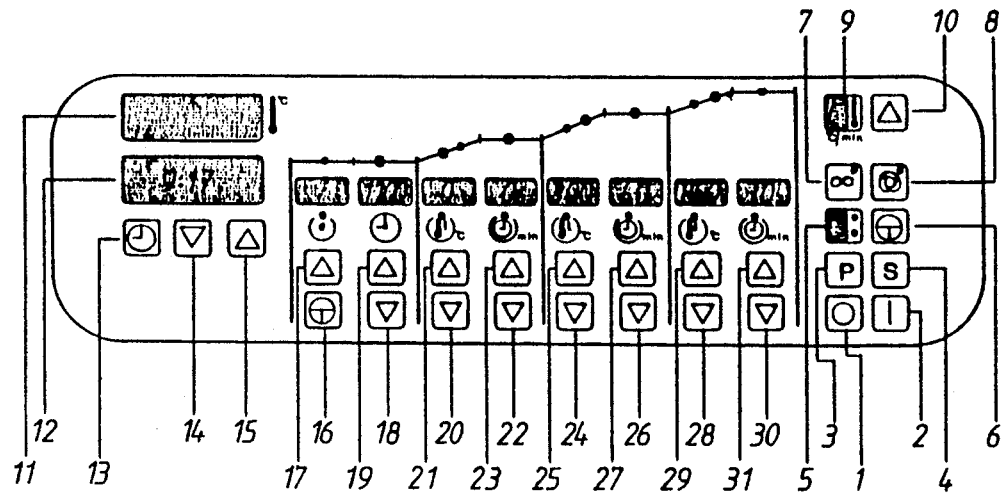
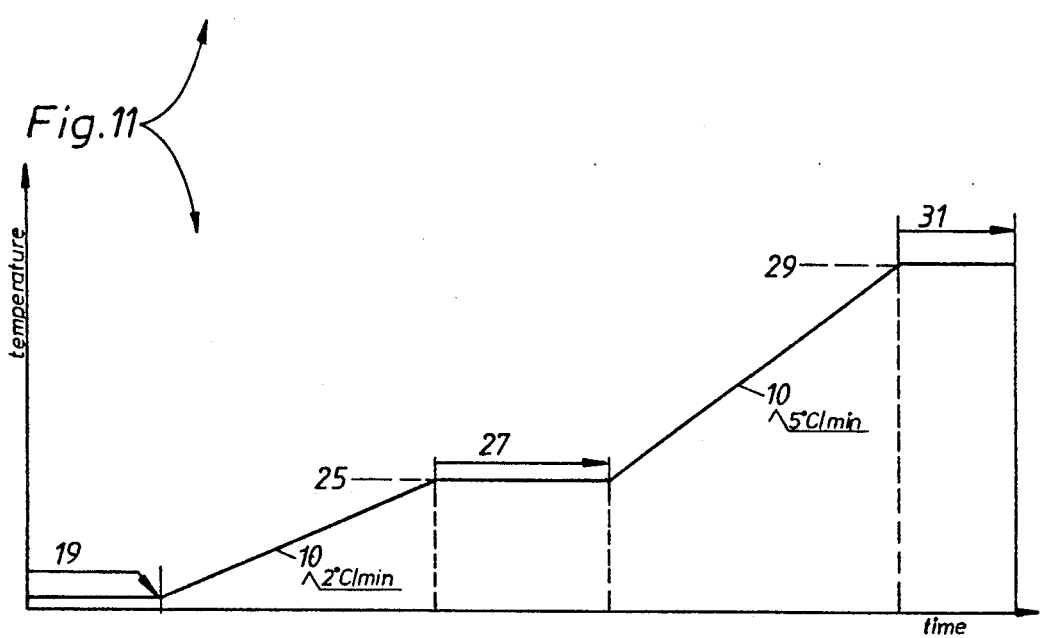
Fig.11

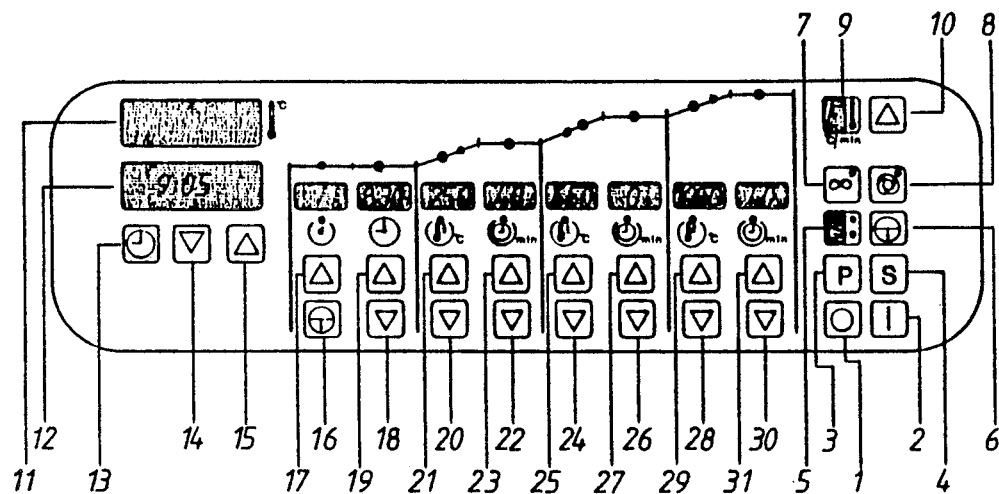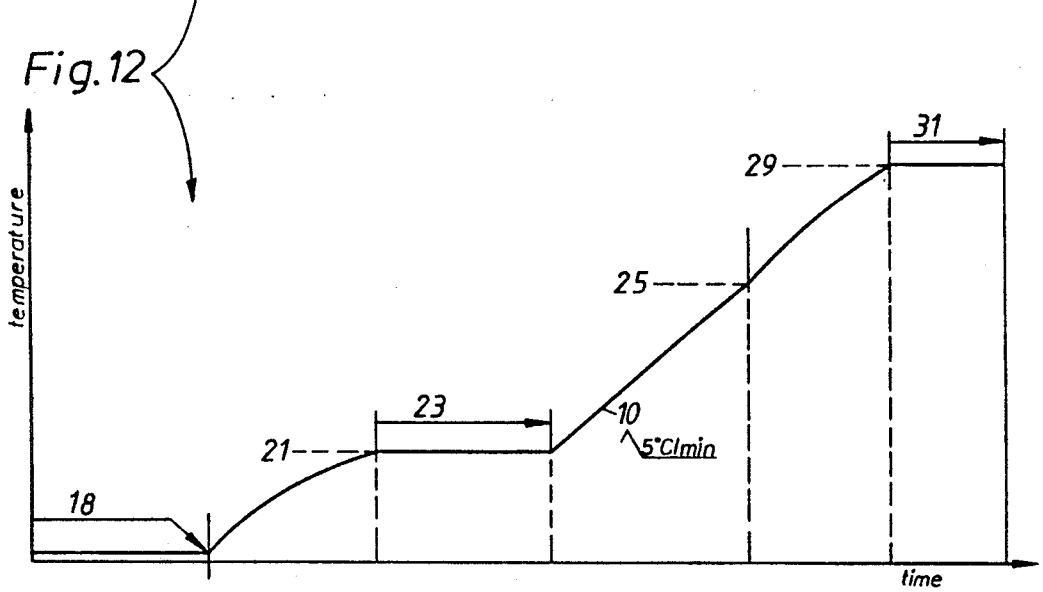
Fig. 12

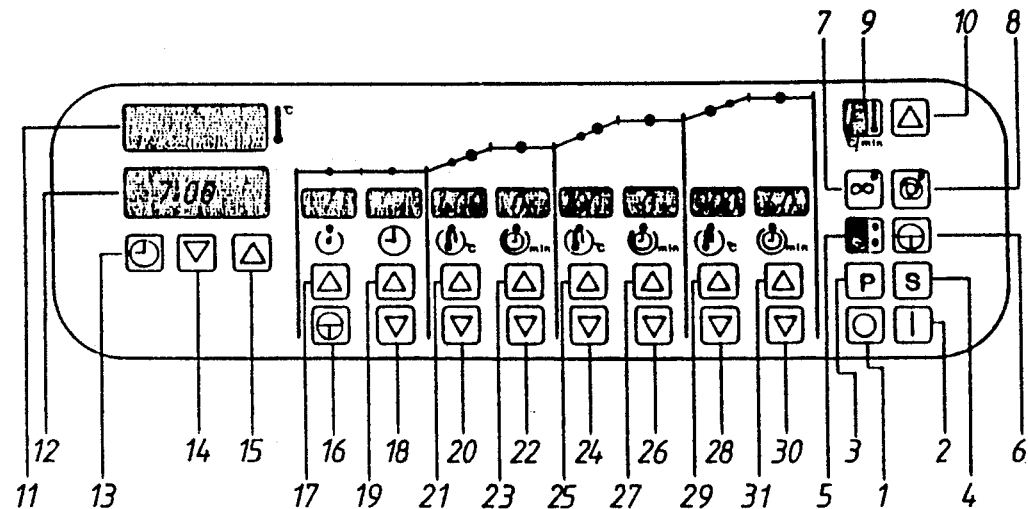
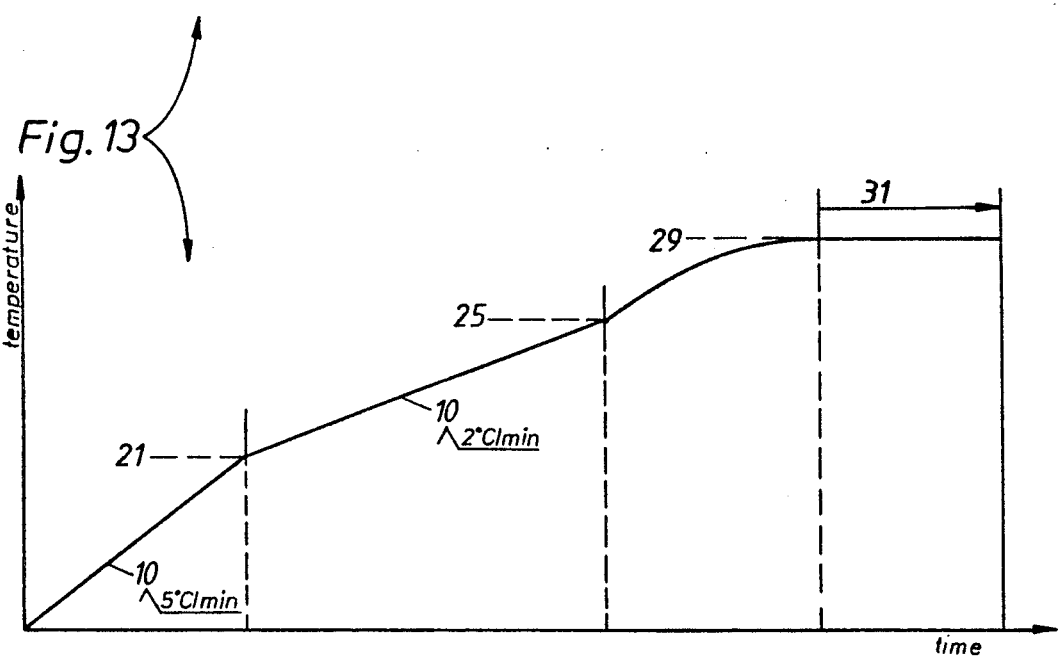
Fig. 13

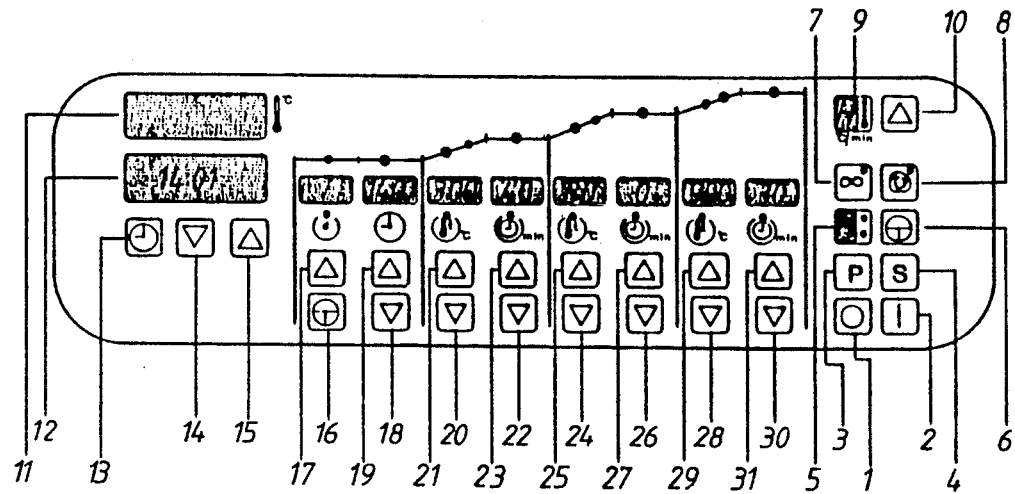
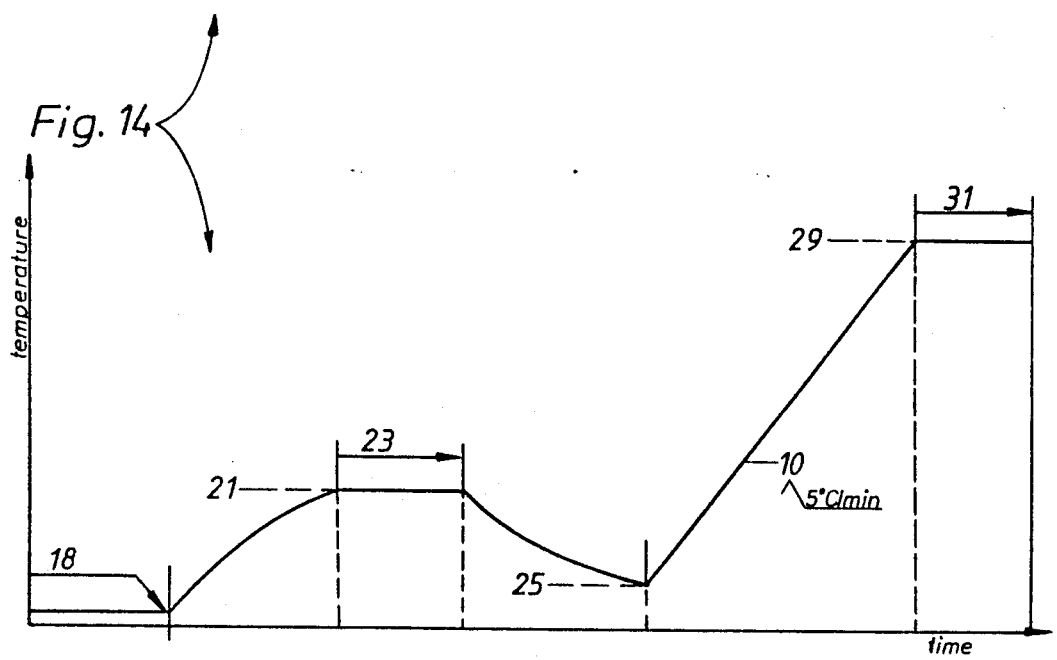
Fig. 14

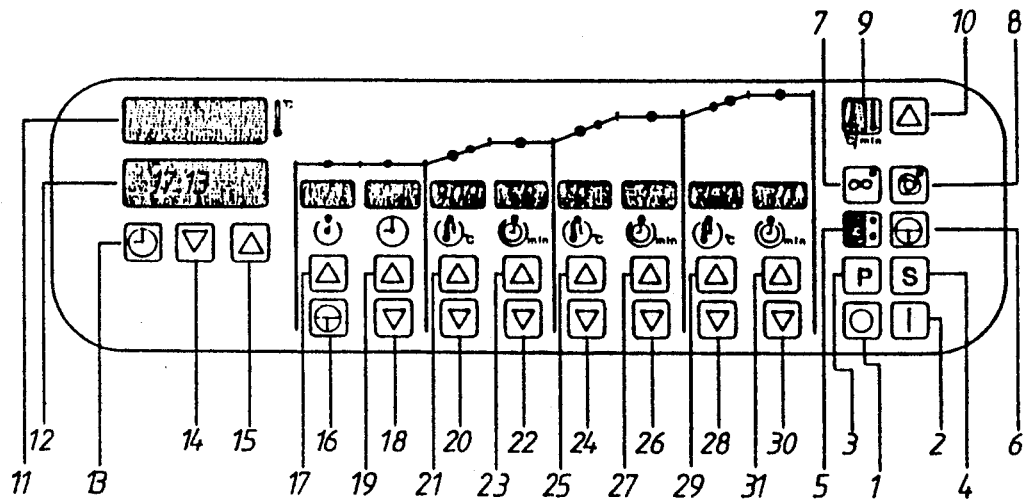
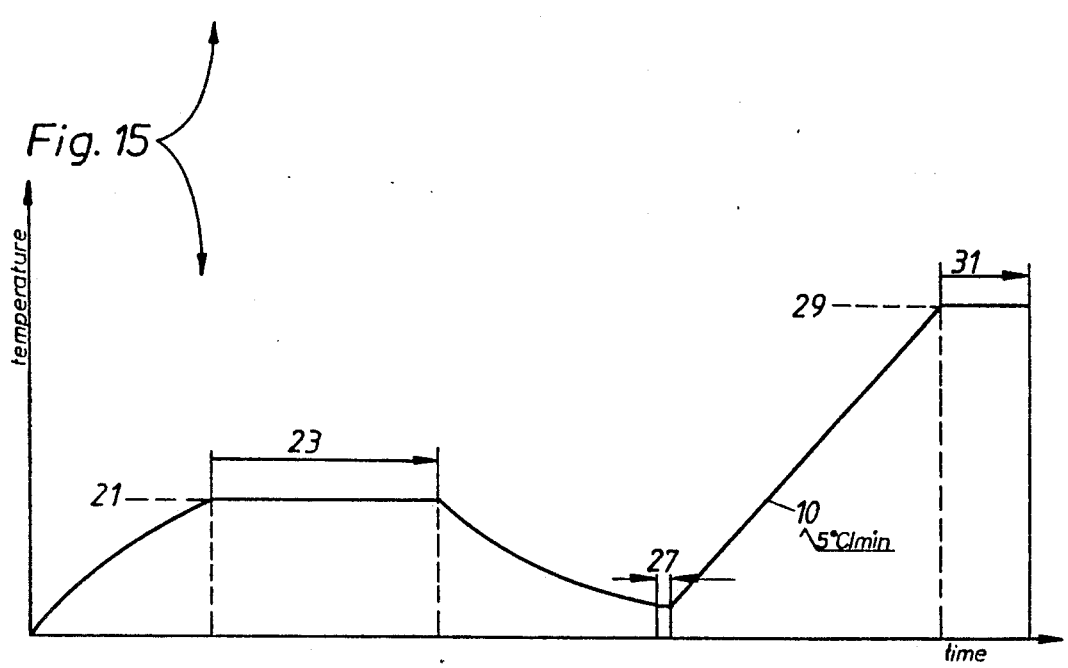
Fig. 15

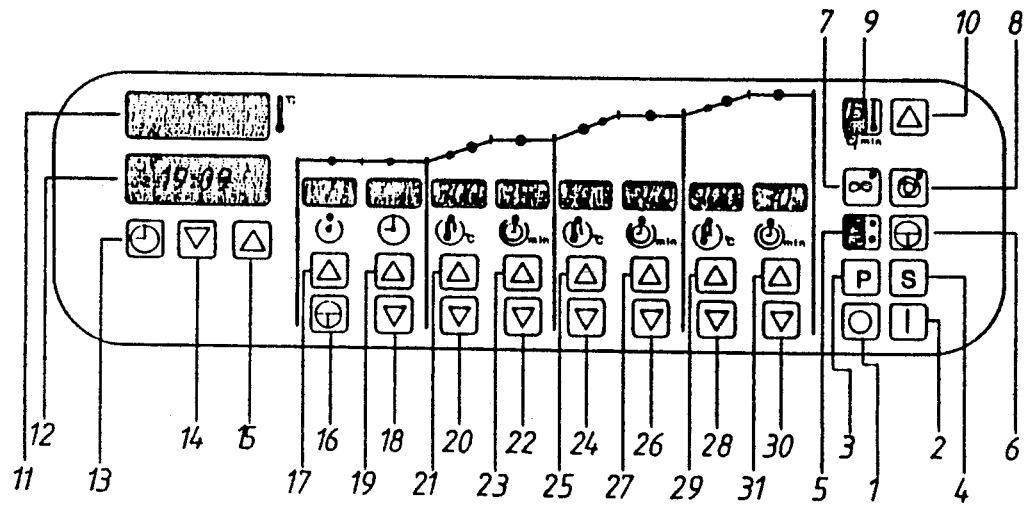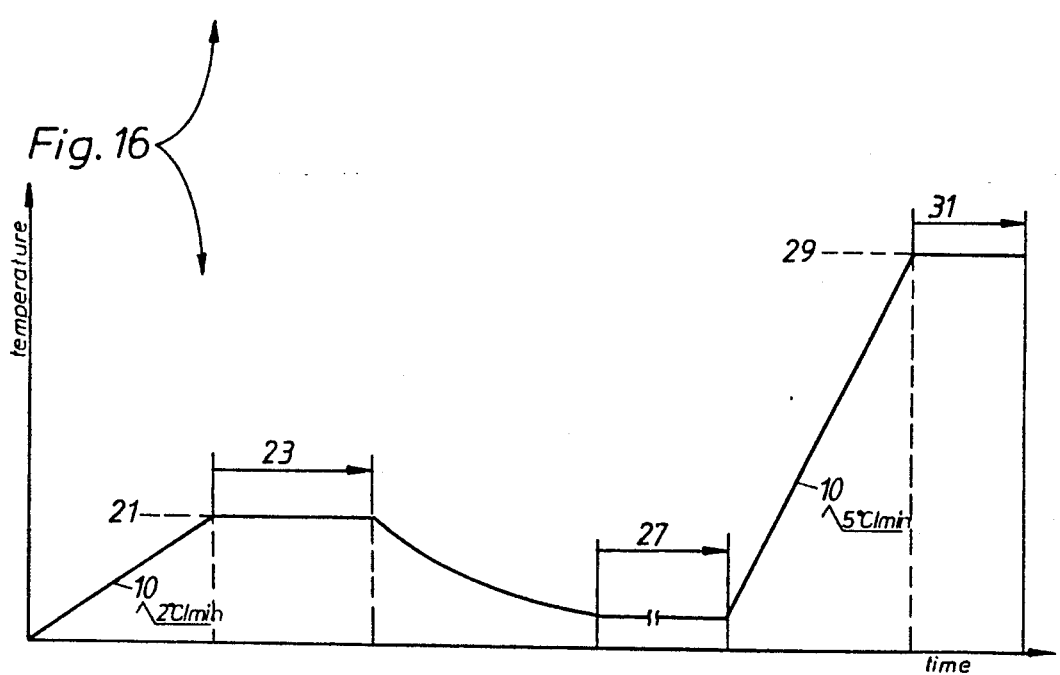
Fig. 16

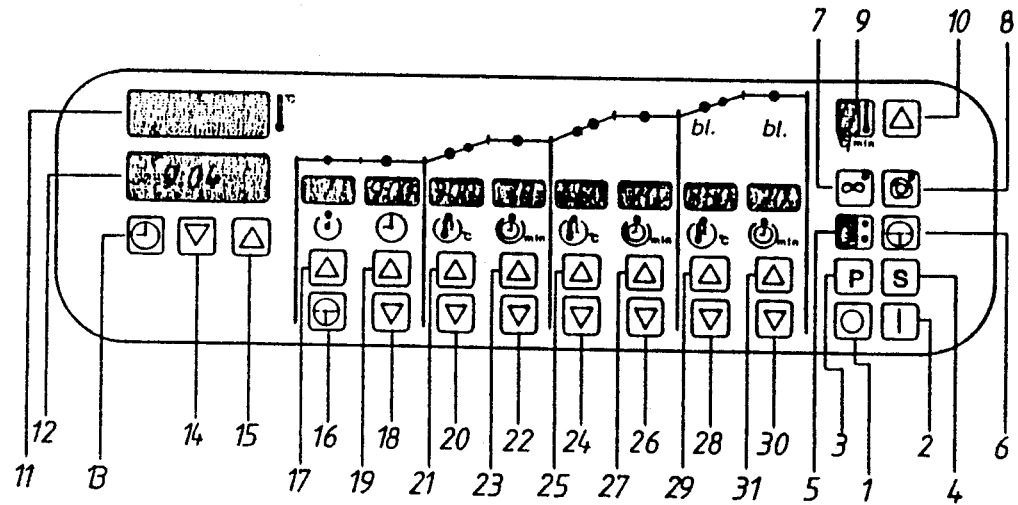
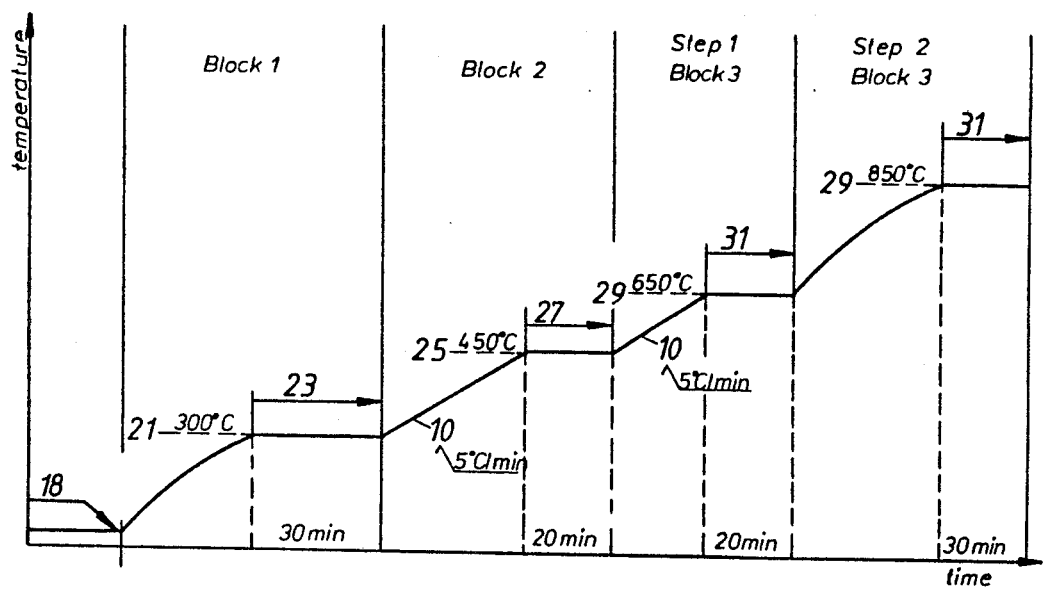
Fig. 17

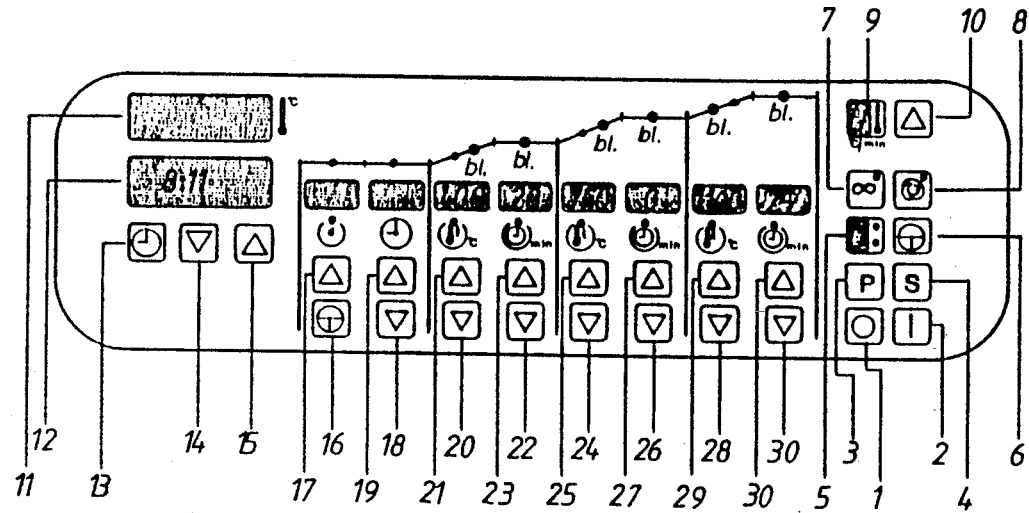
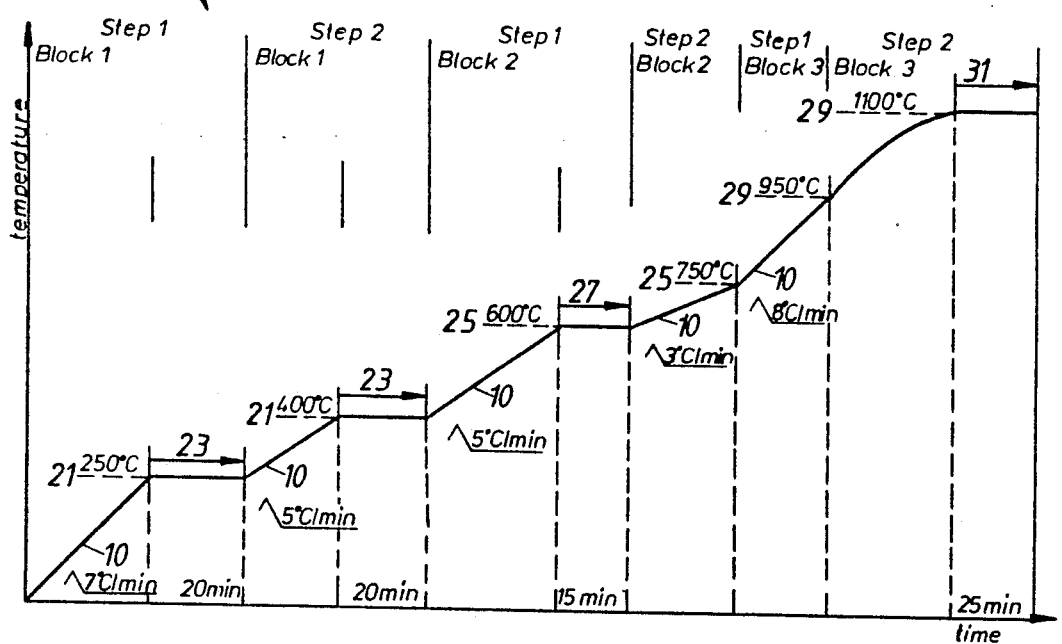
Fig. 18

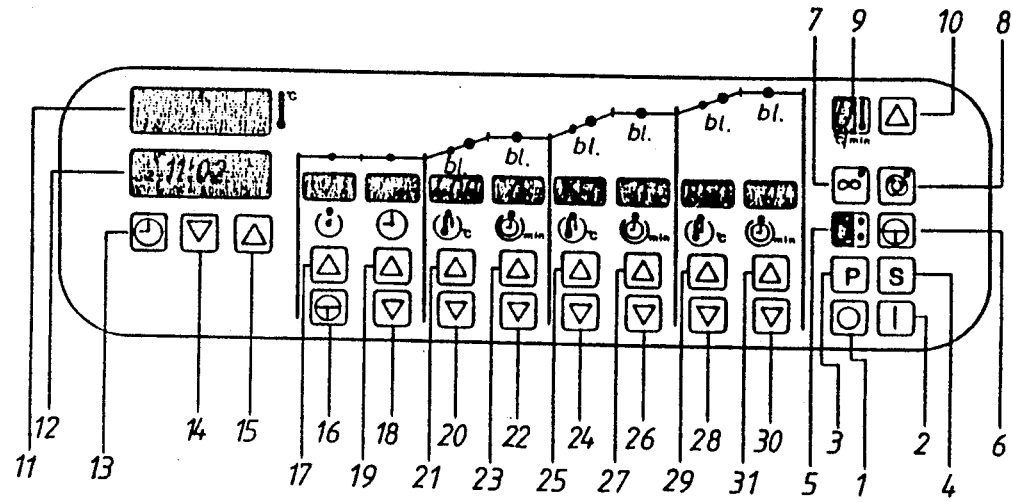
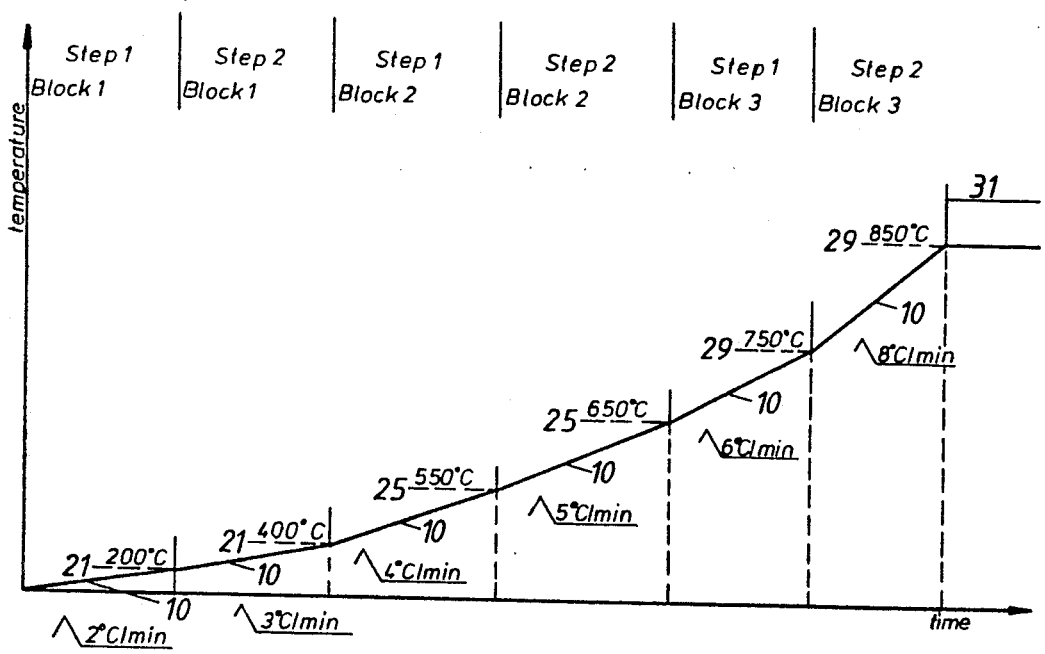
Fig. 19

Fig.22 Numbered Programs

CONTROL ARRANGEMENT FOR DENTAL FURNACES, ESPECIALLY MICROPROCESSOR-CONTROLLED PREHEATING FURNACES

BACKGROUND OF THE INVENTION

1. Field of the Invention

The present invention relates to a control arrangement for dental furnaces, especially microprocessor-controlled preheating furnaces or ovens with controlled heating and with limited rate in the rise of the heating temperature.

Dental furnaces of the above-mentioned type are generally employed as muffle or preheating furnaces for the purpose of preheating goods employed in the dental technology; for example, to preheat casting models which are embedded in the plaster or gypsum-like mass to a temperature which facilitates a problemless or satisfactory flow of the liquified material within even the narrowest passageways. The temperature which is necessary for this purpose is dependent upon the alloy which is employed and, for a casting of noble or precious metal, lies between about 700° C. and 900° C., and for usual precious metal replacement alloys and for model casting lies between about 1000° C. and 1100° C. Inasmuch as the embedding composition is subject to a certain expansion phenomenon, there is mostly required a dwelling period at an intermediate temperature of a magnitude of about 500° C. This intermediate temperature is usually determined on the basis of the so-called Christobalite temperature.

2. Discussion of the Prior Art

In the year 1981, Kaltenbach & Voigt GmbH & Co., Federal Republic of Germany, brought a series of furnaces onto the market, thereby creating the first furnace which, besides the heretofore usual heating with pausing step, facilitated a controlled heating with a specified limited rate in the rise of the temperature. A rising temperature rate of 5° C. per minute was considered to be optimum based on reasons of the material technology. Inasmuch as because of the new series of furnaces the preheating process was substantially improved and became more precisely regulatable, from then on there increased the demands for a preheating of certain embedding compositions which was equal to the system, and became always more complicated. The industry demanded a second and third pausing step, and even a heating sequence with a cooling phase.

Based on experience there was also ascertained that defective castings, which could be traced back to reasons relating to the process technology, could have two different causes; in essence:

1. Errors during preheating; for example, such as an inadequate maintaining of the pausing periods,
2. Error sources in the overall casting system; for example, excessively lengthy delay time between the removal from the furnace until casting or extensive heat reducing absorption by the steel of the casting apparatus.

For the formulation of a new furnace control there was consequently set the task of creating flexible program capabilities in order to be able to realize all currently required and, in the future contemplatable significant program sequences.

Inasmuch as this generates a large multiplicity of different programs, through the utilization of microprocessors the usually complicated input modes should be replaced by a simple and monitorably operable programming keyboard; in effect, the dental technician should be able to introduce new programs or program changes without practically any continual aid from the operating instructions. Predetermined programs which are always repeatedly used should hereby be able to be stored, so as to be called up or retrieved when needed.

SUMMARY OF THE INVENTION

The foregoing object is inventively achieved through a control for dental furnaces of the type described herein, in that the temperature control or regulation is implemented on one or more, preferably three program tiers or levels, with one or more temperature steps or phases being either unrestrictedly or controllably programmed, or implemented on one or more temperature steps in a controlled programming.

Further features of the invention may be more readily ascertained from the following detailed description as set forth hereinbelow.

In general, the size of the control spaces or modules remains the same as heretofore. Inasmuch as the points of connection are the same as those used heretofore, the previous control spaces or modules can be readily exchanged with respect to the new control spaces or modules.

The front plate is equipped with a foil or plastic sheeting keyboard possessing pushbuttons with defined pressure points behind the front or cover sheeting. As a result thereof, the operating keyboard area is a closed or continuous, easily cleanable surface.

In this particular instance, there is created a single basic type of a control space or module for an entire series of dental furnaces. This basic type is apted for voltages of 200 to 249 V+10% to −15%, and 50/60 Hz. The adaptation on three different furnace types with different heating is carried out through the resetting of a DIP switch on an electronic circuit board. Any switching-over of the voltages within this range is not necessary when a suitable electronic device will itself recognize the power supply voltage and automatically sets the applicable regulating parameters; for example, pulse-time encoding for the heating. The same is applicable to the power supply frequency.

For the voltage series of 100 to 130 V+10% to −15%, 50/60 Hz, there can be produced a conversion unit or kit.

In view of the foregoing, the inventive control is universally employable. In the implementation of the invention, there has been considered German Laid-Open Patent Appln. 31 46 391, which discloses a control board for the control or regulating of a dental furnace, which incorporates a power supply switch, setting elements for determining time cycles, a digital indicating or display element for the actual temperature, an indicating element for the time, and a representation of a time/temperature chart, whereby there can be employed known digital setting elements and these then presently clearly associated with the applicable segment of the time/temperature chart. Moreover, each segment of the time/temperature chart has a display lamp associated therewith.

BRIEF DESCRIPTION OF THE DRAWINGS

Reference may now be had to the following detailed description of exemplary embodiments of the invention, taken in conjunction with the accompanying drawings; in which:

FIG. 2 illustrates the conditions on this control board for a first program; and FIGS. 3 through 23 each, respectively, illustrate corresponding conditions for further programs.

DETAILED DESCRIPTION

Figure 1:
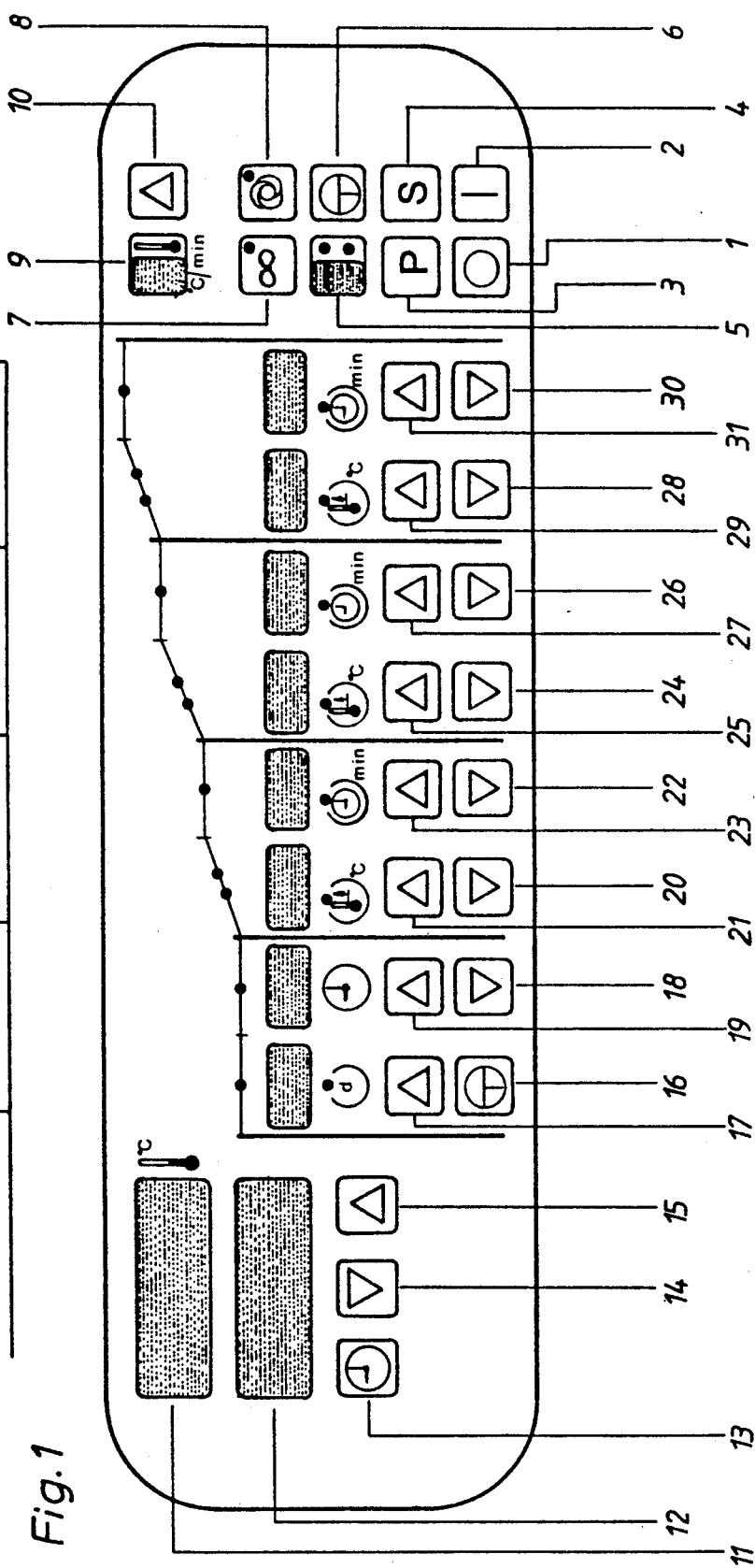
FIG. 1 illustrates a control board for the inventive furnace control.

In FIG. 1, the reference numerals have the following significance:

| | |
|---|---|
| 1 | OFF |
| 2 | ON |
| 3 | P = Program Selection Pushbutton |
| 4 | S = Program Storage Pushbutton |
| 5 | Program Display (green LED's illuminated, as long as program is in progress) |
| 6 | Program Start/Stop |
| 7 | Ventilator CONTINUOUS-operation (LED indicates furn. activated) |
| 8 | Ventilator AUTOMATIC-operation (LED illustrates furn. activated) |
| 9 | Display for limited temperature rise at —° C./minute (dark: full heating power) |
| 10 | Setting pushbutton (forward counting) for restricted rate of temperature rise |
| 11 | Display for furnace temperature, error display |
| 12 | Display for actual time, cycle display of the pausing periods (display counting backward the last 99 minutes) |
| 13 14 15 | Setting pushbuttons for the actual time (for resetting; press 13 + 14 or 15) |
| 16 | ON/OFF pushbutton for lead time |
| 17 | Setting pushbutton (forward counting) for advance; activating delay by 1 to 9 days |
| 18 19 | Setting pushbuttons for input (time) of begin of heating |
| 20 21 | Temperature-setting pushbuttons for 1 st step | Block 1 (for special letter program U: 1 st and 2 nd entered (programmed) step) |
| 22 23 | Time-setting pushbutton for 1 st pausing period | |
| 24 25 | Temperature-setting pushbuttons for 2 nd step | Block 2 (for special letter Program U: 3 rd and 4 th entered step) |
| 26 27 | Time-setting pushbuttons for 2 nd pausing period | |
| 28 29 | Temperature-setting pushbuttons for 3 rd step | Block 3 (for special letter Program U: 5 th and 6 th entered step) |
| 30 31 | Time-setting pushbuttons for 3 rd pausing period | |

The function is as follows:

| ON/OFF PUSHBUTTONS |
|---|
| 1 = OFF |
| 2 = ON |

By means of the ON-pushbutton 2 the furnace is connected to the electrical power supply. Upon the switching-in of the furnace by means of pushbutton 2, the program No. 1 automatically appears in the indicating or display field 5.

Program Call-up and Storage: Program Start and-Stop

Through the pushbutton 3 ("P"), a program can be called up. With every pressure on 3, and continuously displayed under a continual pressure, there appears in 5 the subsequent entered program. When a plurality of programs are not entered or covered by programming, then after the last entered program there appears the next program which is not entered; the remaining programs which are not covered are jumped over. (see "Programming").

With the pushbutton 4 ("S") there can be stored in a program under the program name which is ascertainable in 5 (1-9, A-U). For an acknowledgement that the program storage has been implemented, there is sounded a short acoustic signal. The display field 5 indicates the actual program (program name). With the pushbutton 6 there can be started a called-up or entered, not entered or changed program, or a currently progressing program can be stopped. A short whistling sound is sounded at start and stop.

During a currently running program, all setting functions are blocked, also the time!; with the exception of the ventilator function pushbuttons 7 and 8. The ventilator operation can be changed at any time. When changes became necessary in the program sequence of a started program, then the program must first be stopped by means of pushbutton 6 - a security against any inadvertent changes!, changes! At the renewed starting the program sequence commences again from the beginning.

The fact that a program has started and is in progress, is indicated by the two green LED's in the display field 5. These LED's illuminate continuously during the program sequence. When these LED's blink during the program sequence, this will signal that during the heating phase of the program cycle or sequence, an eventual lead time is hereby not being considered, there is existent a power outage of more than 20 minutes. This power outage can exert an influence over the further processing quality; the user is thereby advised that any defects can be traced back to this as a cause. In this instance, the blinking extinguishes first only with the switching off of the program by means of pushbutton 6 or 1. Stored programs also remain entered at a power outage for so long as the clock battery remains intact (see "Time Display"). A program which is not entered or programmed cannot be started.

Ventilator Control for Suctioning

By means of the pushbuttons 7 and 8 there can be selected the ventilator operation. Through exertion of pressure against pushbutton 7, the ventilator is set on continuous operation (symbol ∞). The yellow LED in pushbutton 7 illuminates. The ventilator is started only with the beginning of the heating program, during any eventual lead or waiting time, the ventilator does not run. A renewed actuation of the pushbutton 7 against switches off the ventilator; the yellow LED extinguishes.

Upon exerting pressure against pushbutton 8, the ventilator is set on automatic operation (symbol ✱). The yellow LED in pushbutton 8 illuminates. With the beginning of the heating program (1st heating step), the ventilator is started and automatically switches off at a temperature of about 700° C. When the ventilator is set to one of the two functions, and the other pushbutton is actuated, then the function switches over in correspondence therewith; for example, from continuous to automatic operation, or conversely. The ventilator is then switched off through a renewed pressing on the activated pushbutton. Inasmuch as the ventilator is for the most part employed in automatic operation, at the call-up of a program which is not entered, the ventilator is automatically preselected to this type of operation (yellow LED in pushbutton 8, is illuminated). In the event that this is not desired, the ventilator can be switched-over or switched off. The ventilator function is a component of a stored program. However, in contrast with all other setting functions, the ventilator can also be changed, switched on or switched off during the program cycle.

Limiting the Rate of the Rise in Temperature

Through the pushbutton 10 the rate or speed in the rise of heating temperature can be limited through integral or whole-numbered values of between 1° C./minute and 9° C./minute; setting being effected through pushbutton pressure, intermittent or continuous pressure, upwardly counting. The set value is indicatable in the display 9. When the display 9 is dark, then the furnace heats with its maximum specific heating power. When heating is effected without any restrictions in the rate of the temperature rise, then during the programming and the carrying out of the program, the red LED is illuminated for the applicable heating step in the program chart; and when heating is effected at a restricted rate in rise of the heating temperature, the yellow LED will illuminate. (For further directions refer to headings "Programs", "Programming").

Indication of the Furnace Temperature

In the display 11 there is indicated the actual furnace temperature in increments of 10° C. A more precise display is not practical because of the total error tolerance, this is accepted in the practice. In this display, in the applicable case, there also appear error indications and control indications (refer thereto).

Time Indication

In the display 12 there is indicated the actual time for a switched-in control space or module (2). During the program sequence, in this display there are also indicated the pausing periods and end dwelling or waiting periods which take place in the program. However, in order to avoid any confusion with the actual time, only the last 99 minutes are displayed counting backwards. When, as is hardly ever encountered in practice, there are introduced periods which are greater than 99 minutes, then with the beginning of the program increment "pausing period" there extinguishes the display 12 and again illuminates as soon as there commence the final 99 minutes. A dark display 12 during the program, in connection with the applicable program sequence display (red LED in the program chart through the applicable pausing period), signals the running of a pausing period whose remaining running time is still greater than 99 minutes. When after completion of the program, switching off is not immediately effected; in effect, when there is no immediate casting, then on this display 12 there blinkingly appears the delayed time after the completion of the program up to the switching off (casting) as a display in minutes with a minus sign in front thereof (maximum −999 minutes, thereafter an overrun display). After the ending of the final pausing period (and dwelling or waiting time) the final temperature is understandably further maintained up to switching off by means of 6 or 1. After the switching off of the program by means of the pushbutton 6 there again appears the actual time.

For the setting or changing of the actual time, also summer time, such as daylight-saving time, the pushbutton 13 must be pressed. By means of the pushbuttons 14 and 15 there can then be set the actual time, either intermittently or by continuous pressure. The requirement that, for the setting of the clock, the pushbuttons 13 and also 14 or 15 must be simultaneously depressed will prevent any inadvertent resetting of the time.

The time setting is powered by a battery during a power outage; in essence, even when the control space or module is no longer connected to voltage, the set actual time will continue running; the life expectancy of the battery, in this instance, for a complete power outage will last approximately 3 to 4 years. However, when the control space is switched off (pushbutton 1), nevertheless, there is voltage present at the clock, auxiliary power must be supplied also only under conditions of a complete power outage.

Such a complete power outage is only encountered in a dental laboratory, except in the case of a malfunction; when the current is completely switched off; for example, during a vacation period. This instance; however, is also encountered when after manufacture of the furnace, under circumstances, the latter must remain in storage for a longer period of time. In order not to use up unnecessary battery capacity in this instance, the clock is switched off after final testing, but, nevertheless, programs remain stored. The clock can be switched off through concurrent pressing on the pushbuttons 13, 16 and 14 in this sequence. Through this three-finger operation there is precluded an unintentional switching off.

When the control space or module is switched on (pushbutton 2), then as a sign that the actual time has been parked the display 12 will light up continuously and show the time 12:00. Through the setting of the clock (by means of the pushbuttons 13 and 14 or 15) the blinking ceases. As a sign of the operability of the time, the two points between the hour and minute display will then blink.

Time Preceding the Begin of Heating

By means of the pushbuttons 16 through 19 the beginning of the heating program can be fixed to a certain time up to 9 days in advance. The time sequence can be a component of a stored program. However, it can be switched on or switched off at any time for a program which has not yet started. The switching on and the switching off is effected through the pushbutton 16.

After the switching on of the furnace cycle, there appears in the display through actuation of the pushbutton 19 the actual time (same time as in display 12). With the pushbuttons 18 and 19, this time can be advanced or set back in minute increments; in essence, upwardly to 23:59, downwardly to 0:00.

As in all pushbuttons possessing counting functions, the values can be adjusted through incremental pressures or through a continual pressure. At a continual pressure, with an increase in the pressure period there increases the setting speed.

When a lead time advance is programmed into the furnace heating, then the furnace commences to heat with the set heating program as soon as the set time as been reached. For example: actual time 14:23; set heating begin: 16:30 - the furnace begins to heat the same afternoon at 16:30 o'clock. Actual time: 14:23; set heating begin: 14:00. The furnace begins to heat on the next day at 14:00 o'clock (as soon as 14:00 has been reached, this is logically the case only on the next day).

In order to be able to determine the beginning of heating a few days hence over a weekend or on holidays, this can be delayed by means of the pushbutton 17 over entire days, by a maximum of 9 days (counting upwardly upon pushbutton actuation of 1 to 9; 0 remains dark). The days for the delay appear in the display by means of the pushbutton 17. When, for example, on a Friday at 17.00 hours (=actual time) there is introduced the beginning of the heating for 5:00 (by means of the pushbutton 19) and two days of delay (by means of the pushbutton 17) and the program is started, then the set heating program does not yet begin to heat on the next morning at 5:00 o'clock, but first only two days later; in effect, on Monday, the display counts backward by means of the pushbutton 17 during the lead time, thus always displaying the still remaining delay in x days. When the display is dark, this means that the oven begins to heat as soon as the time has been reached which has been set by means of the pushbutton 19 (coupled to the actual time in the display 12!).

Based on reasons derived from the control technology, a time selection of 0:00 o'clock (0:00) is not possible! At this setting, the display extinguishes. The input must thus read either 23:59 or 00:01.

The lead time can also be entered through pressure being exerted against the pushbutton 18 or 19. At a pressure against the pushbutton 18; for example, there naturally will appear a time of 1 minute less than the actual time! This type of entry is possible, inasmuch as the pushbuttons 18 or 19 possess a still further function (see hereinbelow).

For the lead time there is thus alwaYs entered the time at which the actual heating program should start.

A programming with respect to the final time; in essence, directed towards the desired casting time, is practically impossible because of the following reasons:

The speed or rate in the heating up of the furnace depends upon the quantity of the filling charge. Theoretically, the dental technician must enter the quantity and what kind of dental flasks and/or flask types he is heating in the furnace. At a controlled heating rate or speed, the computation might be possible through the microprocessor when the heating is carried out sufficiently slowly, inasmuch as the quantity of the flasks would play practically no role. However, when there are programmed within the program sequence one or more temperature rises which are either restricted or with a restriction which exceeds the specific heating power of the furnace in higher temperature regions, then the above-mentioned parameters must be entered, and the heating times which are associated with the applicable furnace type must be present in the basic program, in order to allow for a dependable back-computation or verification.

Notwithstanding the foregoing, in order to facilitate a precise determination for the casting time, the control offers the capability of enabling the entire running time or duration of a program to be read off from the beginning of the heating without considering any eventual lead time prior to heating or furnace actuation until the end of the program; in essence, up to the completion of the last entered program step; any possible delay or waiting period up to the casting is not computed along therewith. Upon exerting a pressure against the pushbutton 18 or 19, there appears in the display, by means of the pushbutton 19, the duration of the program.

The time is displayed for such a length of time, as long as a pushbutton is pressed. When, after the start of the program pressure is applied to the pushbutton 6, 18 or 19 during any possible lead time, there appears 0 minutes.

This program duration is precisely applicable to the conditions which are evident in the present instance. However, they are also reproducible for the same condition since any possible fluctuations in the power supply voltage are compensated for by the electronics. The display of the program duration is effectuated in hours and minutes (for example, 3:32).

Program Progress Indication

In the furnace heating chart above the program function blocks there are provided LED's for every program stage or step. When a program is started, then the applicable LED indicates which program stage or step is instantaneously being implemented or in progress, inclusive the lead time and delay days. During the heating phases there is indicated by a red LED that the furnace is heating at full heating power; by a yellow LED when the furnace is heating at a restricted speed or rate in the rise of the temperature, this value is indicated in the display. When a program has been completed, an acoustic signal will sound, initially at a sounding in 1 minute intervals, then a continuous sound for about 15 seconds. Concurrently, the time display blinks, and there appears in the display 12 the time which has passed (refer to "Time Display"). In the display fields below the program progress chart there stand the applicable set reference values for the applicable program steps or programming guide. For letter programs, these LED's also serve for the programming guide (see "Programming", "Program"). For the special Program U (see therein) the blinking of the program progress LED indicates that this active block is dually entered or programmed and the entered Step 2 is in progress.

Programs

As the main requirement, as is ascertained from the practice, an additional pausing period or holding pause is provided in comparispn with the current controls being marketed by the assignee of the present application, Kaltenbach & Voigt GmbH & Co.

Nevertheless, inasmuch as in the interim, there have already been brought on the market various embedding compositions possessing different heating prescriptions, and there have also been offered for sale furnaces with up to 4 temperature stages or steps, there had to be solved the problem of developing a furnace control which, on the one hand, would be adequate for meeting all demands; in effect, which can be programmed so as to be fully variable, while on the other hand; however, for the large majority of those who merely require one pausing step, it would not become too unwieldly and complicated.

This problem has been solved in such a manner that, for this new control, there is effectuated a programming on three levels or tiers; i.e., three basic possibilities. These distinguish themselves in the simplicity of the programming and the variable configurating of the heating program.

For the subdividing and specifying of the programs, for identification thereof, the first tier is imparted the program designations 1 through 9, and the second and third tiers or levels are imparted the program designations A through U. In effect, there are provided basically "Numbered programs" and "Letter programs".

These programs distinguish themselves in the following manner:

Numbered Programs

These programs possess 9 storage spaces, designated with the numerals 1 to 9.

This program level or tier facilitates a programming in the same manner as the previous control developed by the assignee of the present application, expanded by one pausing step or stage and the capability of operating with pausing periods even under controlled heating.

When a restricted rate in the rise of temperature is selected for a numbered program, then this is applicable to the entire heating program. In essence, all temperature steps or stages are heated at the same restricted rate in the rise of the temperature, or when none is preselected, all steps are heated at full power. A different rate of temperature rise among the individual steps or stages is not possible with numbered programs.

The programming is effected herein principally in the same manner as in the present preheating furnaces; the collective setting values can be monitored at the same time; the sequence of the adjustments is discretionary.

The overwhelming majority of dental technicians operate with these numbered programs.

Letter Programs (except U)

This program level or tier contains 7 storage spaces or modules, designated with the letters A, C, E, F, H, L and P.

Also in this instance it is possible to have a maximum of three temperature stages or steps, whereby on this program tier the rate or speed in the rise of heating can be set to be different in the individual steps; in effect, for example, the first step at a full heating power, second step at a rise of 3° C./min., and the third step at a rise of 5° C./min.

The display 9 and the setting pushbutton 10 are applicable for all steps, the programming is effected in a specified or controlled manner (see "Programming").

The letter programs A through P are similarly simple to program, inasmuch as the programming is controlled or specified from step to step.

Special Program U

This program tier possesses only one storage space or module, defined with the letter U. By means of this special program it is possible to program up to a maximum of six temperature steps. Hereby, each temperature step which is present on the keyboard front plate is dually entered or programmed. As in the case with the other letter programs, also in this instance can the heating rate for each individual step be set differently. The programming is effected in a oontrolled or specified manner (see "Programming"). This program also allows for the programming of relatively complicated temperature cycles; however, in the practice there must be employed a few "specialists". In essence, the three program levels or tiers are assembled such that the so-called numbered program, as is generally adequate in practice, is extremely simple to program and control, practically without the need for any operating instructions.

Programming - Program Control

The programming field of the control arrangement consists of a plastic sheeting keyboard. The pushbuttons each possess a defined pressure point. As a result, the settings can be undertaken through the application of intermittent pressure as well as through continuous pressure. Because of the wide setting ranges, the setting speed is accelerated under a continuous pressure at an increasing (pressing) time in order to be able to derive the shortest possible setting periods. By means of a short release and renewed pressing, the setting again begins slowly. Thus, there can be provided for relatively rapid but still precise settings; eventually with an intermittent pressing towards the end.

The Steps or Stages 1 and 2; for the special Program U the Steps 1 through 4, can be set for up to a maximum of 990° C. and 999 minutes; the 3rd step in the special Program U are the last two steps, up to a maximum of 1150° C. and 999 minutes.

The range for the restricted rate or speed in the rise of the temperature is: 1° to 9° C./min.

At 0° C./minute the display remains dark; in essence, at the full specific heating power of the furnace.

Lead time: Heating begin with real-time input. Furnace begins to heat as soon as the set actual time has reached the next time (controlled by the real-time clock The heating begin is presettable by up to 9 days in advance. When a lead time is set, the red LED's illuminate in the program chart, when no delay step has been set, then only the LED above the actual time.

Program Call-Up

With the activation of the furnace through the ON-pushbutton 2 there automatically always initially appears the Program 1, irrespective as to whether entered or not entered by programming. Through pressing on the pushbutton 3, there can now be called up or retrieved the further programs. Initially, the Numbered Programs 1 to 9, then the "Letter Programs" A through U. However, only the programs which are programmed or entered in the memory storage are called up in addition to the first not entered or stored program of each program tier. As a result thereof, it is not necessary to always scan through all possible programs for the furnace heating sequence.

Program Erasing

In order to preclude an inadvertent erasing of a program, thee is no provision of a pushbutton function "Erasing". Program erasing is consequently of the same significance as program changing. When after effectuating the change, the new program is stored (pushbutton S. 4) then the originally program is erased and the new program is entered.

Should a program be completely erased, then all temperatures of the different stages or steps must be merely set to zero and this then entered. The time periods, in this instance, are automatically set to zero, the ventilator operation similarly automatically changed to "Automatic".

Numbered Programs

All settings can be undertaken in any suitable or random sequence. Nevertheless, it is practical to begin with the 1st step and to program systematically.

When a not yet programmed or entered program is called up, then in the reference value displays there overall appears the 0, the red LED's illuminate in the program chart, and the display 9 is dark. The ventilator operation is automatically set on "Automatic" (yellow LED illuminated in the pushbutton 8). In the display 5 there appears the program number. The lead time remains dark (not set).

Heating Without Intermediate Temperature

In the first and the second temperature step all values are to be set at 0. (20 through 26). The third temperature step is to be set to the end temperature (29) and the dwelling or waiting period (31). Desired ventilator function is to be set; eventually there is to be entered a later heating start (lead time).

When no value is entered with the setting pushbutton 10 (9 remains dark), then the furnace heats at full power, in the program chart the red LED's of the third step are illuminated.

Should heating be carried out at a restricted rate or speed of temperature rise, then the pertinent value is to be entered through the setting pushbutton 10. The value appears in the display 9. As an indication that heating is being effected at a restricted rising rate, in the heating or program chart of the third heating step, analogous to the previous furnace program control, instead of the red there is now illuminated the yellow LED.

The program can then be stored (4) and/or started (6). As a signal for the assumption of the programming in the memory storage and as a starting signal there is presently sounded a short whistling sound.

Heating With One Pausing Step (2 Temperature Steps)

Temperature step value is set to 0 with the aid of the temperature-setting pushbuttons 20, 22. For the two further steps there are to be entered temperatures and times. Value which limits temperature rising rate (10) is to be entered; ventilator functions are to be set; and any possible lead time (16 to 19).

In the program chart there illuminate the LED's of the second and third temperature steps (possibly also the lead time). When no restriction in the rate of the temperature rise is set, the red LED's illuminate in the heating phases, at a restricted rising rate there illuminate the yellow LED's during the two heating phases. The eventual or possible restriction in the rising rate of the temperature is valid for both heating phases, consequently the corresponding value appears in the display 9. Storage and starting as previously.

Heating with 3 Temperature Steps

The intended values for temperature and time in each step are to be set (20 to 31). Any possible restriction in the rising rate (10) are to be entered; ventilator function to be set; and any eventual or possible lead time. In the heating program chart, the LED's of all three steps illuminate.

When no limitation in the rate of rise in temperature is entered (9 dark), then in the heating phases of all three steps there will illuminate the red LED's. When the rate in the heating rise is restricted, then in the heating phase of all three steps there illuminate the yellow LED's. Since the restriction is then equally applicable to all steps (numbered program), the value appears in the display 9.

Heating with Cooling Phase

Temperature and pausing period to be entered for 1st step (21, 23).

Cooling Phase in a 2nd Step: Temperature to be set to which it is to be cooled down. When a temperature is set of less than 60° C., then the furnace is nevertheless only cooled down to 60° C. Upon reaching 60° C., the program proceeds with the next step.

The reason: Assuming the room temperature is at 30° C., and 20° C. was entered as the cooling temperature, the program would no longer be implementable, inasmuch as this temperature would never be reached. Since in warmer countries there can be expected room temperatures at over 40° C., the threshold level is set at a higher value.

Temperatures of higher than 60° C. were implemented. A pausing period can be entered and is then also implemented. A further possibility consists of permitting the temperature of the second step to remain at 0. However, in that case, the pausing step must be set to a duration of at least 1 minute. When both values of the second step are left at 0, then this step is suppressed, inasmuch as it is then recognized as not being covered or existent. Accordingly, in order for a step to be implemented, there must be entered at least one value which is greater than 0! Step 3 can be programmed in a known manner.

Letter Programs A through P

Program designations: A, C, E, F, H, L, P.

When one of these letter programs is called up, and this program is not yet entered or programmed, then the three steps are called up in sequence.

Initially, the two LED's of the first step illuminate in the program chart (20 through 23). In the reference value display of this step, the 0 always appears. The display 9 remains dark, however, a point blinks in this display. The two remaining steps are dark.

When no setting pushbutton is actuated, then in the same manner the display changes after about 5 seconds to the Step 2 (24 to 27), and after a further about 5 seconds changes to Step 3 (28 to 31). After 5 seconds there again illuminate all red LED's in the program chart, overall in the reference value displays there is indicated "zero"; in 9 there is shown the program name (for example, A; the same as in 5), ventilator operation is again on "Automatic" (yellow LED in 8 is illuminated); lead time is dark.

The programming can then be carried out in such a manner, that a short-term pressing is exerted against a suitable pushbutton of the first step. There lights up or illuminates again only the first step, and the values of this step can be entered. With the exertion of the first pressure against a pushbutton there is thus at first activated the step, the values of this step are then set only by means of the second pressure. When for this step there is entered a restriction in the rate of the temperature rise; for example, through the setting pushbutton 10, the value is then indicated in the display 9, and in the program chart, within the temperature rising region there will illuminate the yellow instead of the red LED's. This restricted rate in the temperature rise, in contrast with the numbered programs, is valid for this step only. In this step, when there is no longer undertaken any setting for about 5 seconds, the display will then change (program chart, reference value display) to the next step. For this and the third step, the same programming procedure is applicable: When for a period of about 5 seconds there is no longer effected any setting, then the program will always switch to the next step.

When all steps have been passed through, then all corresponding LED's of the individual steps will commonly illuminate, and the reference value displays indicate the entered values. Hereby, an exception is formed by the display 9. Hereby, in that in the letter programs, in contrast with the numbered programs, every step can be carried out with differently restricted rates in the rise of the heating, this display does not show any value at the entire program value display, but shows the letters of the program designation or name. Whether one of the steps is programmed with a restricted rate in the temperature rise can be recognized from the program chart; in the rising region there is then illuminated the yellow LED of this step. For a started program, the value of each step is naturally indicated in the display 9.

The programming procedure need not basically begin with the 1st step. Each step can be individually called up through the exerting of a short pressing action against any one of the pushbuttons of this step. Through a renewed pressing, values can be entered or changed.

The further step change is effected commencing from this active step. When, after the last input of a step, there is immediately activated another step, there is then eliminated the 5 second waiting period.

Naturally, upon effectuating the program call-up for the first time there is no need to wait until the collective step changes are completed, but immediately can programming be implemented with the first step, or any suitable activated step. A step whose two values of temperature and time are each set on zero, is considered as not being entered or existing, the displays of these steps extinguish. For example, when a not yet entered or non-existent program is called up, then "zero" appears in all steps. When thereafter in one step a value; for example, the temperature, is raised to 10° C. and subsequently again reset to zero (time=zero), then this step is extinguished! When both values for temperature and time are zero, it is also impossible to have an input for a restricted rate in temperature rise, an eventually or possibly entered value is extinguished; the display 9 becomes dark.

Program Call-Up

When a stored program is called up, the program call-up proceeds in a manner such that, beginning with Step 1, each step is indicated for a period of approximately 5 seconds (reference value for temperature, time and type of heating). Upon heating with full heating power, in the rise of the power chart for the applicable step there illuminates the red, and for a restricted rise in temperature the yellow LED (value in 9). After the third step all values are indicated, and the program letter appears in the display 9. If any one pushbutton of a step is pressed once, then the values of this step are displayed, inclusive 9; and then, after approximately 5 seconds, the subsequent step. Moreover, after a program has been started, it is possible to call up or retrieve collective program values. Temperatures and times of all existent or covered steps are visible in the reference value displays. When pressure is exerted on any one of pushbuttons 10 or 20 through 31, there is effected a complete program call-up, beginning with Step 1. In the display 9 thee can then be determined the rate or speed in the temperature rise which is associated with each step. At a call-up during the time of a continuing or running program, the steps which are not programmed or entered are jumped over.

Special Program U

Special Program U, as can be ascertained from the program names or designations, is a letter program. It distinguishes itself from the other letter programs in that every step can be doubly entered or programmed. It is thereby implementable with a maximum of 6 temperature steps.

In comparison with the remaining letter programs A through P, the following association is applicable:

| Letter Programs A-P | Setting Pushbutton | Special Program U | Program Sequence LED's |
|---|---|---|---|
| Step 1 | 20-20 and 10 | Step 1 + Step 2 | continually illuminated blinking |
| Step 2 | 24-27 and 10 | Step 3 + Step 4 | continually illuminated blinking |
| Step 3 | 28-31 | Step 5 + Step 6 | continually illuminated blinking |

The recognition as to which of the two possible steps of each setting block is currently being programmed, called-up or activated during a program cycle, is carried out with the aid of the program sequence-LED's. Every first entry or programming of a block; in effect, all odd-numbered steps, are indicated through continually illuminated LED's; every second entry or programming; in effect, all even-numbered steps, through blinking LED's. This is applicable during a program retrieval or call-up, as well as during the programming, and during the program call-up while a program is in progress as well as for the display during the program sequence.

At the call-up of the Special Program U (by means of the program selection pushbutton 3, P) there is thereby initially displayed the 1st block. First, there appear the values for the 1st step (when restricted rate in temperature rise correspond to value in the display 9). The LED's of the 1st block in the program chart illuminate continually. When no value is entered or changed, then after approximately 5 seconds there appear the values of the 2nd step, whereby the LED's of the 1st block will blink. When after approximately 5 seconds, no pushbutton is further actuated, there the appears the next step; in effect, the 3rd step. The LED's of the 2nd block illuminate continually. After approximately 5 seconds without any actuation there appears Step 4, the LED's of the 2nd block will blink. During the following Step 5, the LED's of the third block again illuminate continually during the values-display, blink at the values of Step 6.

When the entire program steps and their values are indicated in this manner, then in the displays there presently appear the second programmed or entered steps in every block, signaled through blinking LED's (in the display 9 there stands a "U", analogous to the remaining letter programs). As a result, there is already provided optical information that the Special Program U has been called up or retrieved with the dual entry or programming of the blocks (steps).

Understandably, not all steps need be entered or programmed. In a block, when only one step is entered, then after the call-up there appears, in the program display, this entered step with the applicable temperature and time values, whereby the LED's of this block will then continually illuminate independently as to which step is entered or programmed in this block.

At a renewed call-up of the program; for example, through a touching or tapping against one of the pushbuttons of the 1st block, this block appears again in the programmed sequence. At an interrogation of the program during the program sequence; for instance, through the touching of a pushbutton of this block, then this step also also appears again in the entered or programmed sequence.

Also, during the program sequence, the applicable LED indicate in the program chart as to whether an even-numbered or odd-numbered step is entered or programmed. When, for example, Step 1 is not programmed and Step 2 of the 1st block is programmed or entered, then the applicable LED's of the 1st block will blink during the program call-up, upon the value call-up during a program sequence, and during the program sequence itself when the program is located in this stage or step.

After passing through the program call-up, in effect, when the entered value for temperature and time of the individual steps appear; however, the LED's would not blink as evidence that this block is only singly programmed.

In the Special Program U, in the total display of the blocks, in essence, subsequent to passing through the value display of the individual steps, there is indicated through continually illuminated LED's in the blocks that such blocks are only singly entered or programmed independently as to which step of this block is programmed. Through the blinking of the LED's there is indicated that the associated block is dually entered or programmed. In this case there is indicated the second; in effect, the even-numbered step of this block. In this manner, there can also be immediately recognized as to how many temperature steps are contained in the program (continually illuminated LED's=1 step in this block; blinking LED's=2 steps in this block). For example, when all three blocks are entered or programmed with only one step, then there appear all temperature and time values as an overall display; in the display 9 there is shown U, and all LED's of the cycle diagram illuminate continually, independently as to which steps of the blocks are entered or programmed. This corresponds then optically to the other letter programs, which is also logical throughout, inasmuch as such a program is operatively so as also readily be able to be entered or programmed into the Letter Programs A through P. Only for a dual entry of a block does there appear, in the "Total" display, the blinking of the LED's (display value of the second step of this block) as an indication that, in this block, there are entered or programmed both steps.

The manner in which these two steps are programmed can again be determined in that a pushbutton within this block is touched or tapped. The value of even step will then appear for a period of approximately 5 seconds.

When not all steps are entered in the program in Special Program U, and there is undertaken a value call-up during the progress of the program sequence after the starting of the program, then the steps which are not entered or programmed are jumped over. When in one block; there is existent, for example, only the 2nd step is covered or entered, then pursuant to the state of the control technology, this step can without difficulty be "slid" into the 1st step. However, this would signify a program change. By permitting this sequence to remain, in front of this step there can be easily inserted a further step; for instance, with a lower temperature, and possibly again be erased. During the shifting of the steps this would no longer be possible; the entire block would have to be newly programmed. Except for this capability of the dual entry or programming of each block, the Special Program U conforms with the remaining letter programs.

1st Example

Heating with 4 Temperature Steps, 4 Pausing Periods and Different Rates in the Rise of the Temperature (see FIG. 17)

2nd Example

Heating Program with Six Temperature Steps, 4 Pausing Periods and Different Rates in the Rise of the Temperature (see FIG. 18)

3rd Example

Heating Program with Cooling Phase to Approximately Room Temperature, Thereafter Heating Without Pausing Period Final Temperature with 4 Further Temperature Steps and 3 Pausing Periods; Different Rates in the Rise of Temperature (see FIG. 19)

4th Example:

With the Special Program U it is possible to practically reverse the physically required heating curve of the furnace which extends pursuant to an e-function, in effect, initially rapid, then increasingly slower; and to allow the furnace to heat at an increasing heating rate.

Program with increasing rates in the temperature rise for the heating and 1 final dwelling period. (see FIG. 20)

Warning Indication-Automatic Correction

With the exception of a few special instances, there is programmed in the dental laboratory a heating program with rising temperatures and mostly also including pausing periods.

When subsequent to a temperature step there is provided a further entered or programmed step with a lower temperature than the previous step, or the time period for a step set to zero, this can be either completely intentional or, however, can also be imported to a programming error. In this instance, the user is warned during the storing of the program 4, as well as during the starting of the program 6. Prior to the storing or the starting of the program, those temperature inputs will blink which, within the sequence of the program, are lower than those of the preceding step. In the same manner, all time settings will blink which are set to zero. Through this warning indication, the user should be put on notice as to any possibly existing incorrect programming. The blinking lasts for about 5 seconds. After these 5 seconds there is carried out the storing or, respectively, starting of the program, as long as no corrective action as been undertaken.

When, within a first temperature step which is to be carried out, the temperature is set to zero but there has been set a time which is greater than zero, this would be illogical inasmuch as in that instance the point in time for the activation has been merely shifted by this amount of time.

EXAMPLE

.The selected activating timepoint is 8:00 o'clock (setting pushbutton 19). The 1st step is programmed with 0° C. and a 10 minute pausing period. This would signify that the actual commencement of the heating would be carried out at 8:10 o'clock. This programming is not sensible and merely renders more difficult the surveyability of the program, especially for letter programs, and above all for program U.

Consequently, such a program is not accepted. In this instance, the time is automatically corrected to zero, and thereby this step is considered as not entered or programmed (step becomes dark, at a program call-up there twice appears zero). This; however, is always only applicable to the first programmed or entered temperature step. For example, when Step 1 of the program is not entered (temperature and time=zero), and when for the second step the temperature=zero and the time set greater than zero, then also this step (first entered step) is corrected.

Passed Delay Time Display

After the completion of a program; in effect, after the completion of the last pausing period (final dwell time), on the time display 12 there blinkingly shows the zero. Concurrently, there sounds an intermittent sound (whistling sound) as an acoustic indication. After one minute, the intermittent sound changes to a continuous sound of approximately 15 seconds in duration, and in the time display there is now indicated the time which has passed since the end of the program as traversed time with a minus sign in front thereof. This display blinks continuously. When the maximum indicated passed time= −999 minutes, then there appears the overrun time .

Warning Signal At Lengthier Power Outage

In the event that, during the course of the program, there is encountered a power outage for a lengthier period of time, this is signaled through a continuous blinking of the green LED's in 5 (blinks, until program is switched off). Considered herein is a power outage lasting more than 20 minutes. Shorter power outages, in general, do not exert any excessively great influence on the work, inasmuch as the thermal inertia of the entire system is relatively considerable.

Program Progress Period

The running time or progress period of a started program can be retrieved or called up.

Measured is the time from the beginning of the heating of the 1st temperature step up to the end of the program; in effect, until the last pausing period has been passed through. Any possible prior lead time and waiting time at the end of the program are not measured therewith.

Upon pressing on pushbutton 18 or 19, there appears in the display through the setting pushbutton 19 the time period calculated in minutes commencing with the start of the heating. After passage of the pausing period of the last temperature step there can thus be read off the entire running time for the program. The display in 19 appears as long as one of the pushbuttons 18 or 19 is pIessed and again extinguishes shortly after the release. The time is extinguished with the switching-off of the program (1 or 6). At a power outage, the time for the outage of the power supply is not counted, the time counts further after the connecting-in of the power supply. The power outage does not set the time back to zero.

Constant Heating Power

Through an automatic power output correction there is compensated for any fluctuations in the supply voltage. Consequently, the furnace heats constantly at the same specific heating power within the respective voltage ranges of 100 to 130 V and 200 to 240 V. Program cycle or running periods thereby remain practically constant. Under circumstances, differences are encountered for the same program due to considerably different equipping.

Coding Control

At the actuation of the furnace with the aid of the pushbutton 2 there is automatically effected a control as to whether the control space or module is correctly coded for the furnace type and the supply voltage. Immediately after the actuation there appears on the display field 11 the furnace type (this is shown on the front plate of the control panel; for example, 5636) and in the display field 12 the average supply voltage of the applicable supply voltage range. For the range of 200 to 240 V there is thus indicated 220 V, for the range of 100 to 130 V there is indicated 110 V. The display is maintained for approximately 1.5 seconds, then there appears the actual time and Program 1. When the indicated furnace type and voltage do not conform with the furnace and voltage range, this signifies the presence of a coding error, or an incorrect control module has been installed.

Monitoring the Operational Readiness of the Furnace

The furnace control is equipped with an automatic self-control device for certain operational components. Operational errors, incorrect servicing, electronic and display malfunctions are recognized and displayed. The error display is carried out in the display field 11 through the blinking of the letter E and a characterizing numeral. A characterizing numeral characterizes the error and thus facilitates the customer service department and possibly an outside repair service of providing the most rapidly possible assistance, without requiring the furnace to be returned for repairs.

The following errors are recognized and displayed:

| | |
|---|---|
| E 1 | Door not closed, the furnace cannot heat in this instance due to the safety switch-off. |
| E 2 | Thermoelement effective (sensor breakage) |
| E 3 | Thermoelement incorrectly poled. |
| E 4 | Malfunction in the heating circuit, hereby either the heating can be interrupted (heat conductor breakage) or there can also be encountered continuous heating (short-circuit of triac). |
| E 5 | Triac does not switch (Triac defective or activation defective). |
| E 6 | Power supply relay defective; for example, welded contacts. |
| E 7 | Clock battery exhausted, incorrect actual time; stored programs are lost. |
| E 8 | Coding error (control space on DIP-switch S 174/S 175 not yet coded to the furnace type). A control as to whether the control module is correctly coded is automatically carried out upon the connecting of the control module (see 14). |
| E 10 E 11 E 12 | Malfunction in the electronic components. service information required, serves for the rapid locating of malfunctions during repair. |
| E 90 E 91 E 91 Blinking actual time | Clock switched-off or impossible time display (for example, 33:00 o'clock, or the like). |

Teaching Aid for New Furnaces

The furnaces are delivered with entered or stored program examples. These programs should be components of the service manual so as to provide a practical foundation for the user in support of the theoretical explanations. These programs can naturally be changed or erased by the user. They are then lost.

Test Program

The control arrangement is equipped with a permanently built-in test program. This test program serves, above all, to recognize errors during manufacture, and in the case of repairs to be able to localize the error source as rapidly as possible without any extensive measuring or testing requirement. This program can naturally also be employed by the technical customer service, in order to be able to recognize certain malfunctions without any measuring or testing demands. Thus, with the aid of the available test program; for example, without necessitating the use of testing or any special technical know-how, there can be determined as to whether all pushbuttons within the plastic sheeting keyboard operate satisfactorily, whether all LED's inclusive the points in the value displays (for example, the clock are operable, and above all, if the collective 7-segment displays indicate satisfactorily (control of all individual segments).

The test program serves for the testing of diverse hardware components and for the display of a few internally programmed computational values. The test program is permanently built into the program EPROM.

The call-up or retrieval is effected through a specialized pushbutton combination in order to preclude any inadvertent call-up. Moreover, the call-up can only be effected during normal operation (no heating program is running).

Software-Construction

The control modules which are each equipped with a program which corresponds to the foregoing description, are provided with the electronic characterization Version 1. Upon the actuation of the furnace 2, for a short time there appears in the display through 19 the code for the program-Version 1: 1.00. Thereby, this renders visible which program version is currently present. Should, due to any reason, it becomes necessary to implement a change in the program, then this would be assigned the next code-numeral.

Procedure During the Programming

Since all values are visible on the displays during number programming, in this instance a systematic procedure is not absolutely necessary. However, it is recommended that, even in this instance, should the values which are to be set should be previously permanently recorded in writing. This can be carried out on a program sheet in accordance with an enclosed sample. This sheet can also serve as a program monitor; for example, when a plurality of different programs are required; for instance, different quantities, multiple users each with their own programs, and so forth.

With regard to the letter programs, it is urgently recommended to provide a prior permanent written record in order to avoid any errors, and after completing the inputs of the entire program to again be able to test the later for correctness. During the programming of letter programs, the following procedure is recommended:

First enter the temperature and time values of all steps. Then, only at a renewed passing through, enter the limited pausing period for each step. As a result, the temperature and time values of each step can once again be controlled. Thereafter, set program ventilator function and possible lead time.

In FIG. 2 there is represented the Program No. 1 on the control board and the time/temperature chart.

Program No. 1

Furnace begins to heat on the second day (1 day later) at 5:00 o'clock. Heats at full power (9 dark) to 50° C. and maintains this temperature for 60 minutes. Ventilator is on "Automatic" operation 8.

Program not yet started (LED's in 6 are dark and in the program chart all entered values are displayed).

FIG. 3 is a representation relating to Program No. 2.

Program No. 2

Furnace begins to heat the next morning at 5:00 o'clock. Heats at a restricted heat rising rate of 5° C./min. until 850° C. has been reach and maintains this temperature for 60 minutes. The ventilator is not in operation.

FIG. 4 relates to Program No. 3.

Program No. 3

Furnace begins to heat on the next day at 13:00 o'clock (actual time 13:05, 13:00 o'clock only occurs again on the next day).

Furnace heats at full power (9 dark) to 250° C., maintains this temperature for 40 minutes, then heats at full heating power to 700° C. and maintains this temperature for 30 minutes. The ventilator is on continuous operation.

FIG. 5 relates to Program No. 4.

Program No. 4

The furnace begins to heat at 15:10 o'clock (after 10 minutes). The furnace heats at a restricted temperature rising rate of 3° C./min. to 250° C. and maintains this temperature for 40 minutes. It then heats further at a rising rate of 3° C./min. to 700° C. and maintains this temperature for 30 minutes. The ventilator is not in operation. Since the restricted rate of temperature rise is equally applicable to both steps, the value is displayed in 9 - number program.

FIG. 6 relates to Program No. 5.

Program No. 5

The furnace begins to heat on the next morning at 6:00 o'clock, heats at full power (9 dark) to 250° C., maintains this for 40 minutes, then again heats at full heat power to 600° C., maintains this for 45 minutes and heats then similarly at full heating power to 850° C. and maintains this for 30 minutes. The ventilator is on "Automatic" operation.

FIG. 7 relates to Program No. 6.

Program No. 6

The furnace begins to immediately heat at a restricted rate of temperature rise of 5° C./min. to 250° C., maintains this for 30 minutes, then again heats at 5° C. /min. up to 600°, maintains this for 40 minutes, and then again heats further at 5° C./min. up to 900° C. which temperature is maintained for 60 minutes. The ventilator is on "Automatic" operation. The heating rate of 5° C./min. is equally applicable to all three steps - value is displayed in 9.

FIG. 8 relates to Program No. 7.

Program No. 7

The furnace begins to immediately heat at a restricted rate of temperature rise of 4° C./min. to 250° C., maintains this for 40 minutes and then cools down to about 60° C. After 1 minute the furnace heats further at 4° C./min. to 700° C. and maintains this for 30 minutes. The ventilator which is in "Automatic" operation also runs during the cooling phase.

When the pausing period of the 2nd step is also set to zero, then both values of these steps are not entered or programmed. The control arrangement would then recognize these steps as not being entered and suppress them. The furnace would then not cool down in the 2nd step, but immediately heat further with the 3rd step.

In order for a step to be implemented, one value of the step must always be higher than zero.

FIG. 9 relates to Program No. 8.

Program No. 8

The furnace begins to immediately heat at a restricted temperature rising rate of 4° C./min. up to 250° C. This temperature is maintained for 40 minutes. Thereafter, the furnace cools down to about 60° C. and then again heats at 4° C./min. to 700° C. and maintains this temperature for 30 minutes. The ventilator is on "Automatic" operation, it also runs during the cooling phase. When no restriction in the temperature rising rate (9 dark) is entered or programmed, then the furnace will heat at full power during both heating steps. When a cooling temperature of 1 < 60° C. is entered, there is then generally cooled down to a furnace temperature of 60° C.

When a value of >60° C. is entered, there is then cooled down to the selected value.

FIG. 10 relates to Program A.

Program A

The furnace begins to heat at 5:00 o'clock on the next day. Heating is effected in the 1st step to 250° C. at full heating power (red LED through 21). This temperature is maintained for 40 minutes. Thereafter, there is further heated to 600° C. with limited rising rate (yellow LED through 23, value 3° C./min. (program call-up)). The temperature of 600° C. is maintained for 30 minutes and then there is heated further at 5° C./min. (yellow LED through 29, value through program call-up) up to 850° C., which is maintained for 30 minutes. The ventilator is on "Automatic" operation.

FIG. 11 relates to Program C.

Program C

The furnace begins to heat on the same day at 11:00 a.m. Step 1 is not entered or programmed. Temperature and time = zero in the displays; when set to zero, possible dark displays. Furnace heats at rising rate of 2° C./min. (value is determinable through program call-up) up to 300° C., maintains this for 40 minutes and then heats further at 5° C./min. (value determinable through program call-up) up to 800° C. and maintains this for 30 minutes. The ventilator is on continuous operation.

FIG. 12 relates to Program E.

Program E

The furnace begins to heat on the next day at 8:30 o'clock. The furnace heats at full power to 250° C. and maintains this temperature for 40 minutes. Continued heabing is then effected at 5° C./min. (yellow LED, value through program and call-up) up to 650° C., thereafter without any pausing period at full heating power up to 1050° C. This temperature is maintained then for 40 minutes. The ventilator is on "Automatic" operation.

FIG. 13 relates to Program F.

Program F

The furnace begins to heat immediately at 5° C./min. (yellow LED, value in 9 through program call-up) up to 400° C., and then heats further without any pausing period at 2° C. /min. up to 700° C., and from there without any pausing period at full heating power further up to 900° C. This temperature is maintained for 40 minutes. The ventilator is on continuous operation.

FIG. 14 relates to Program H.

Program H

The furnace begins to heat on the next day at 14:00 o'clock. Heating effected up to 300° C. with full heating power, temperature maintained for 40 minutes, thereafter cooling down effected to 80° C. If in this case there had been entered, for example, a room temperature of 20° C., the furnace would cool down to about 60° C. As soon as 80° C. has been reached, the furnace heats at 5° C./minute (yellow LED, value in 9 called-up by program) up to 900° C. and maintains this temperature for 30 minutes. The ventilator is on "Automatic" operation.

FIG. 15 relates to Program L.

Program L

The furnace begins to heat up immediately at full heating power up to 300° C. and maintains this for 50 minutes. Thereafter the furnace cools down to about 60° C. and maintains this temperature for a period of 1 minute. This time is necessary since the temperature of this step was set at zero. If the time of this step were also set to zero, then this step would be ignored; in effect, would not be implemented. After this cooling phase, the furnace heats at a restricted rate of rising temperature of 5° C./min. up to 750° C. and maintains this for 30 minutes. The ventilator is on "Automatic" operation and runs during the program sequence for so long until about 700° C. has been reached; also during the cooling phase.

FIG. 16 relates to Program P.

Program P

The furnace begins to heat immediately at a rate of 2° C./min. up to 300° C. and maintains this for 35 minutes. Thereafter, cooling is effected to approximately 60° C. The furnace then remains at this temperature for about 4 hours. Thereafter, heating is effect at 5° C./min. to 900° C. and the temperature maintained for 30 minutes. The ventilator is set on "Automatic" operation.

FIG. 17 relates to Program U.

Program U

The furnace begins to heat on the next day at 5:00 o'clock. Heats a full heating power to 300° C. and maintains this temperature for 30 minutes. Heats further at 5° C./min. to 450° C. and maintains this for 20 minutes. Thereafter further heating is effected up to 650° C. at 5° C./min. and maintained at this temperature for 20 minutes. Then heating up to 850° C. with at heating power and maintaining the temperature for 30 minutes. The ventilator is on "Automatic" operation.

In the overall board display the values of the 1st programmed step of block 3 ( = 3rd heating step) are not recognizable as such. The blinking of the LED's of this block in the program chart; however, indicates that this block ls dually programmed. All values of both programmed or entered steps of the block 3 can be called up through the tapping on of one of the pushbuttons of this block (28 through 31). At first there then appear the values of the 1st programmed step of the block inclusive 9 (continually illuminated LED's in the program chart) and after approximately 3 seconds the values of the 2nd programmed step (blinking LED's).

The continuously illuminated LED's of the blocks 1 and 2 indicate that these are only singly programmed. The value for the rate of rising temperature in block 2 (yellow LED) is obtained through touching or tapping one of the pushbuttons of this block (24 through 27). It appears in 9. In accordance as to whether the 1st or the 2nd programmed step is entered, these values appear with continually illuminated or, respectively, blinking LED's. The values of the other programmed steps show zero or, respectively, remain dark during a call-up after the start of the program.

FIG. 18 relates to another type of the program U.

The furnace begins to heat immediately at 7° C./min. After reaching of 250° C. this temperature is maintained for 20 minutes. Thereafter, the furnace heats at 5° C./min. up to 400° C. and maintains this for 20 minutes. Further heating is effected up to 600° C. at 5° C./min. and this temperature is maintained for 15 minutes. Thereafter, there is again heated up to 750° C. at 3° C./min. (without any pause up to 750° C.) and then up to 950° C. at 8° C./min. (again thout any pause up to 950° C.). From 950° C. on there is heated at full heating power up to 1100° C. and this temperature is maintained for 25 minutes. The ventilator is set on "Automatic" operation.

In the overall board display, in all three blocks the LED's blink in the program chart; in essence, indicating that all three blocks are dually programmed. There are indicated (in a stationary condition) the values of the 2nd, 4th and 6th block; in effect, always the second programming of a block (at a dual programming), in there appears the letter U.

The values of the not displayed programmed steps can be obtained through tapping against any one of the pushbuttons of the applicable block. When, for example the pushbutton 20 is touched or tapped for a short time, then initially there is initially displayed the programmed Step 1, Block 1 (constant), then the programmed Step 2, Block 1 (blinking) then the programmed Step 1, Block 2, and so forth. When, for example, the pushbutton 30 is touched for a short time, then initially there is shown the programmed Step 1, Block 3, and then the programmed Step 2, Block 3. There is also displayed, always commencing with the called-up block, this block and the following blocks.

Upon tapping or touching any one pushbutton while the program is being implemented; in effect, with the furnaces in operation, there is always displayed the entire program.

FIG. 19 relates to a modification of the Program U.

Figure 20:
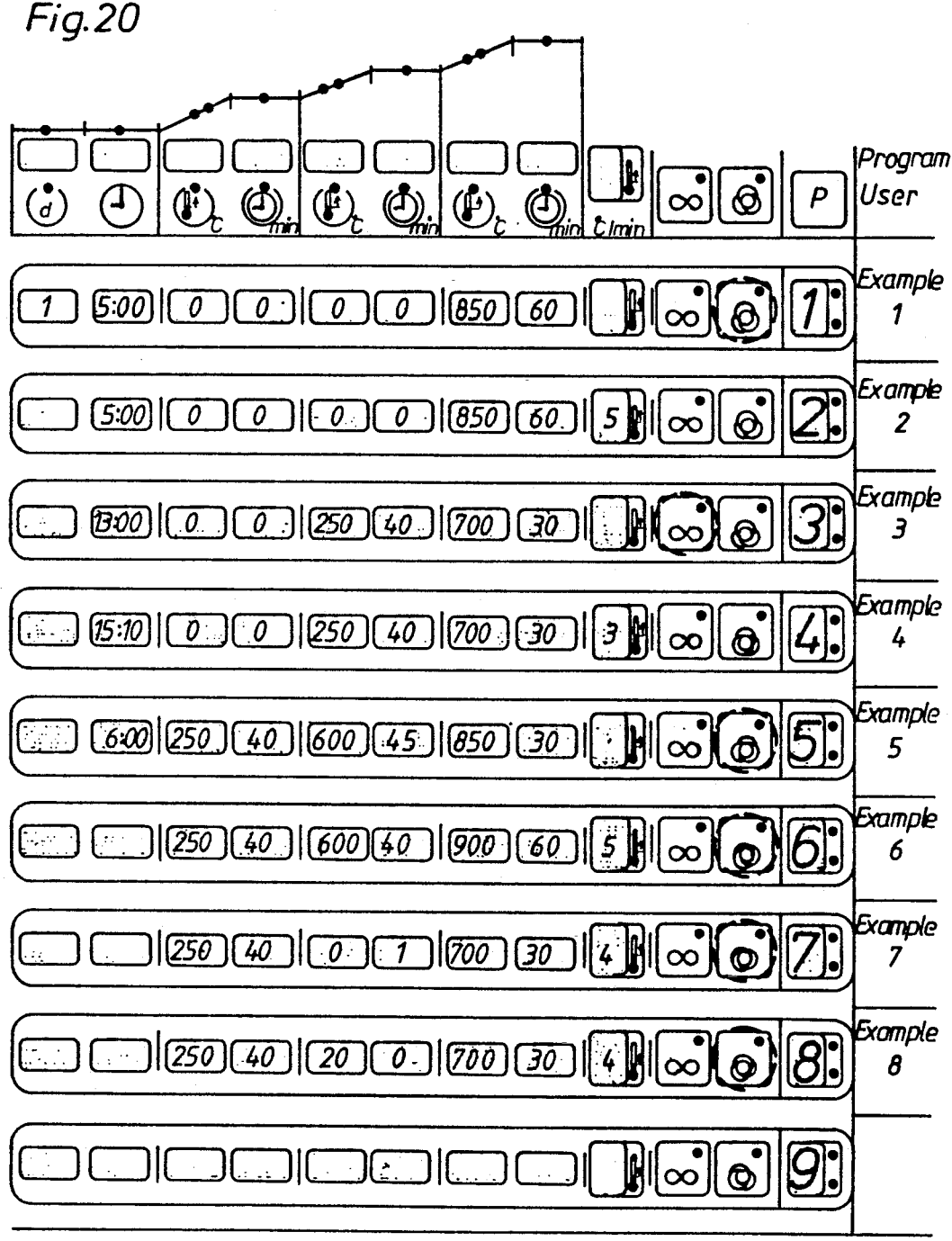

FIG. 20 illustrates displays on the control board for the numbered programs.

Figure 21:
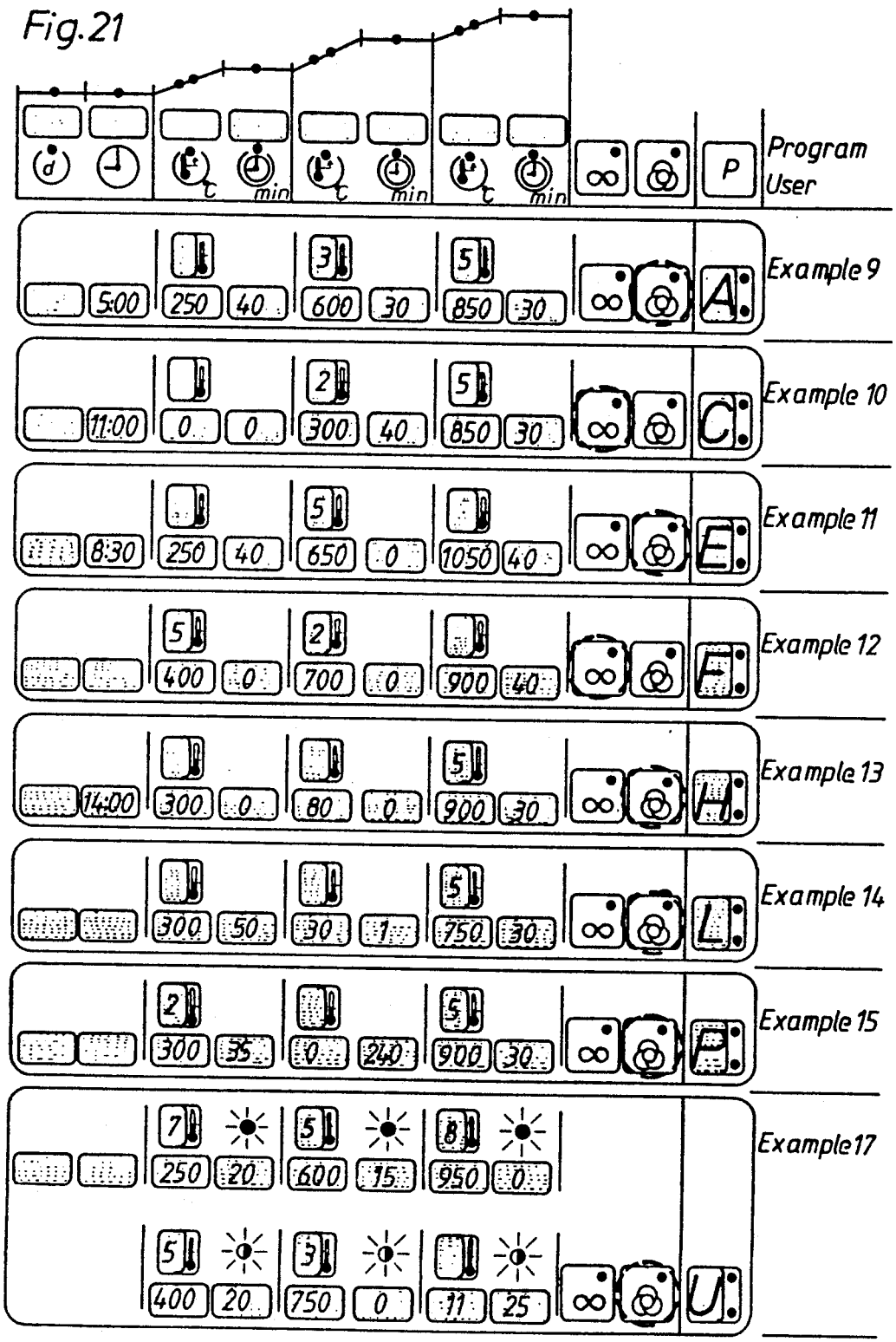

FIG. 21 illustrate displays on the control board for the letter programs.

Figure 22:
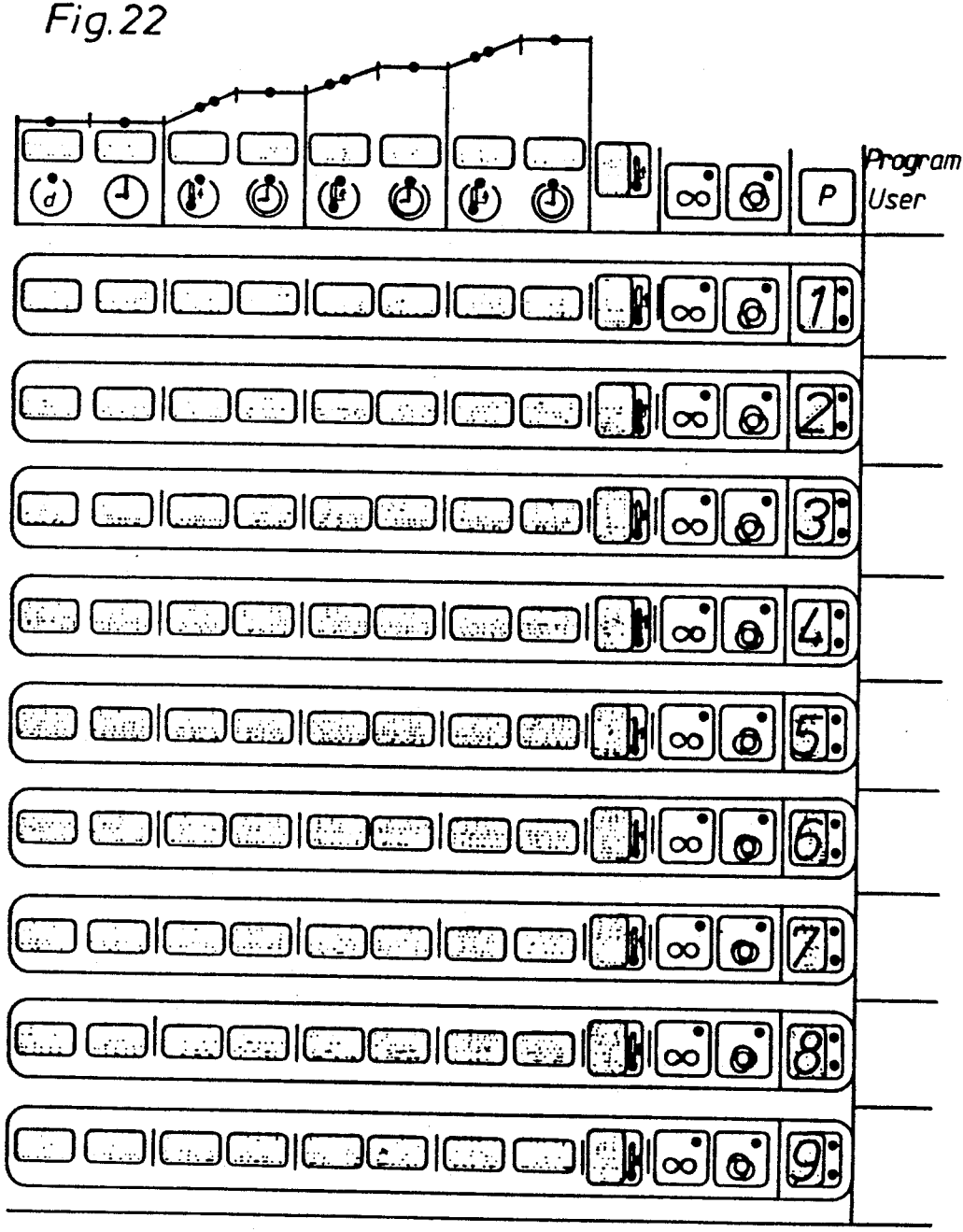

FIG. 22 illustrate displays for the numbered programs.

Figure 23:
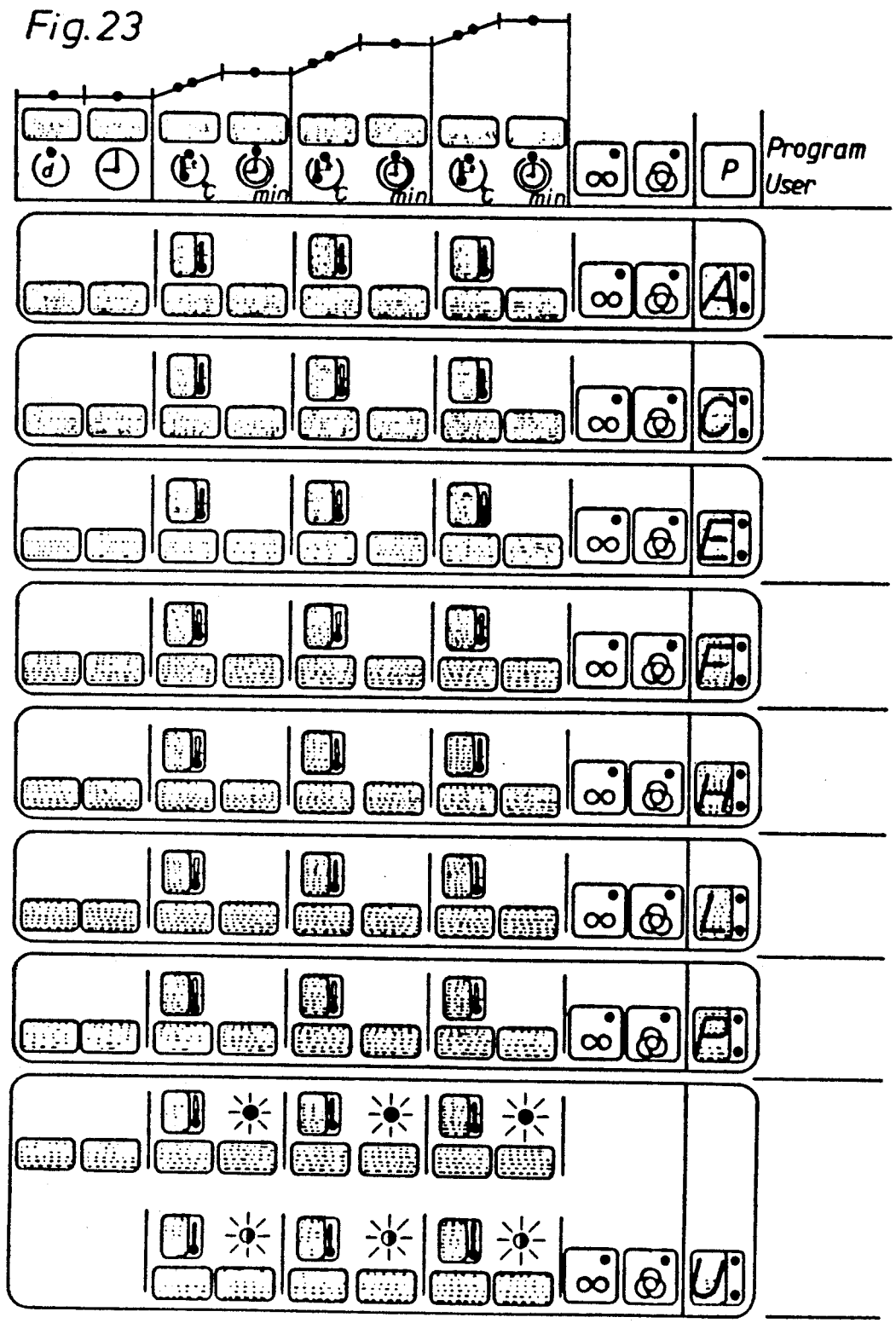
Figure 24:
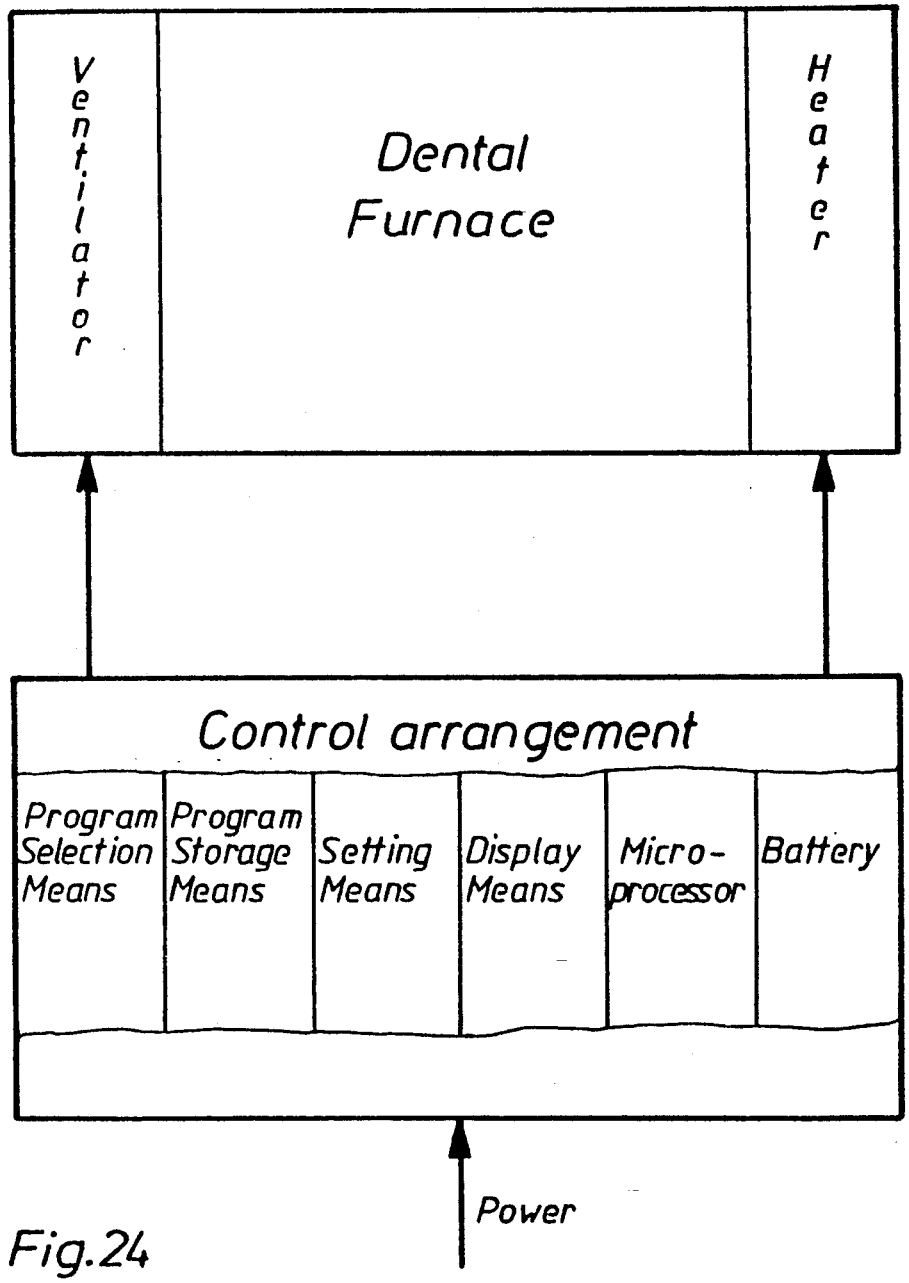
FIG. 24 illustrates the control arrangement.

FIG. 23 indicates displays for the letter programs.

What is claimed is:

1. A control arrangement for controlling the heating of a microprocessor-controlled heating dental furnace having restricted rates in the rise of temperature in the dental furnace, including a program selection means for selecting heating program stored in a memory means associated with the microprocessor, an input means for programming and storage in the memory means of the rate in the rise of the heating temperature and pausing periods after predetermined temperatures are reached, and a display means for displaying an indication of a seleted heating program and also for displaying the process of a selected heating program by individual display elements relating to a curve representation comprised of a predetermined number of individual heating periods and pausing periods, characterized in the provision of individual display elements for said curve representation and setting elements (16 to 19; 20 to 23; 24 to 27; 28 to 31) for setting the individual heating periods and pausing peiods, by the setting of which a heating program can be changed and a particular heating program can be selected for storage in the memory means, and in which during a heating program including additional heating periods and pausing periods exceeding the predetermined number of heating periods and pausing periods in the curve representation, at least one display element of one of the periods represented in the curve representation indicates and displays the course of the additional heating and pausing periods.

2. Control arrangement as claimed in claim 1, wherein the temperature control is effected with one to three temperature steps.

3. Control arrangement as claimed in claim 1, wherein the temperature control is effected with up to 6 temperature steps with controlled programming.

4. Control arrangement as claimed in claim 1, wherein the rate of heating speed is restrictable on the first tier or in each individual step on the second and third tiers to 1° to 9° C./minute.

5. Control arrangement as claimed in claim 1, wherein a control board incorporates a programming arrangement including direct association of setting and display elements with individual steps of a time-temperature chart.

6. Control arrangement as claimed in claim 1, wherein reference values of all steps are displayed during the program sequence.

7. Control arrangement as claimed in claim 1, wherein said program is locked in during the progress of the program.

8. Control arrangement as claimed in claim 1, wherein a ventilator is operated in continuous automatic operation under automatic preswitching during programming.

9. Control arrangement as claimed in claim 1, wherein the beginning of a heating program determinable up to nine days in advance through an input of actual time.

10. Control arrangement as claimed in claim 1, wherein the settable temperature can range up to 1150° C.

11. Control arrangement as claimed in claim 1, wherein the pausing periods for individual steps is settable up to 999 minutes.

12. Control arrangement as claimed in claim 1, wherein the accumulated pausing periods commencing from 99 minutes of resting time are displayed counting backwards.

13. Control arrangement as claimed in claim 1, wherein real time is displayed as long as no pausing periods are running.

14. Control arrangement as claimed in claim 1, comprising a program sequence display for recognition of a selected individual heating program.

15. Control arrangement as claimed in claim 1, including an optical or acoustic signal for signalling the end of the program.

16. Control arrangement as claimed in claim 15, wherein said optical or acoustic signal is initially an intermittent optical or acoustic signal, followed by a continuous sound-emitting signal or a blinking display.

17. Control arrangement as claimed in claim 1, wherein an acoustic control signal is generated upon the storing of a program, which is indicative of storing of the program in the memory means.

18. Control arrangement as claimed in claim 1, wherein the duration of the program sequence is retrievable.

19. Control arrangement as claimed in claim 1, wherein a signal is generated indicative of a lengthier power outage during a program sequence.

20. Control arrangement as claimed in claim 1, wherein an optical display indicates the delay time commencing from the end of the program.

21. Control arrangement as claimed in claim 1, including an actual-time display with power outage battery replacement.

22. Control arrangement as claimed in claim 1, including securing the program during a power outage.

23. Control arrangement as claimed in claim 1, including an optical display for indicating restricted rates of rise in temperature at program call-up and during the program sequence.

24. Control arrangement as claimed in claim 1, including time-accelerated value setting responsive to exerting continued pressure on a keyboard possessing pressure points.

25. Control arrangement as claimed in claim 1, including a warning indication for a potentially erroneous programming prior to a storing or starting of the program.

26. Control arrangement as claimed in claim 1, including an automatic correction at an illogical programming.

27. Control arrangement as claimed in claim 1, including compensation fluctuations in a power supply voltage.

28. Control arrangement as claimed in claim 1, including control monitoring and display for operational, electronic and display errors and malfunctions, and for a remote diagnosis thereof.

29. Control arrangement as claimed in claim,1, including a furnace type and coding control responsive to actuation of the furnace.

30. Control arrangement as claimed in claim 1, including a display indicative of a dual programming on the third temperature tier for a selected program.

31. Control arrangement as claimed in claim 1, including a teaching aid at delivery of the furnace provided by stored program examples.

32. Control arrangement as claimed in claim 1, including a test program for localizing errors and malfunctions, such as through remote diagnosis.

33. Control arrangement as claimed in claim 1, including a closed, dust protected and easily cleanable plastic sheeting keyboard.

34. Control arrangement as claimed in claim 1, including a simulation circuit for providing a time-accelerated simulation of a particular program sequence.

35. A microprocessor controlled heating dental furnace with controlled heating, including an unrestricted rate in the rise of the heating temperature, and limited restricted rates in the rise of the heating temperature, with the microprocessor being programmed to control the temperature of the dental furnace on at least one of three program tiers, with the first program tier comprising a number of programmed temperature steps which are heated at the unrestricted rate, or at the same restricted rate, and the second program tier comprising a limited number of programmed temperature steps which can be heated at different restricted rates in the rise of the heating temperature, and the third program tier comprising a number, greater than said limited number, of temperature steps which can be heated at different restricted rates in the rise of the heating temperature.

* * * * *

UNITED STATES PATENT AND TRADEMARK OFFICE
CERTIFICATE OF CORRECTION

PATENT NO. : 5,072,360

DATED : December 10, 1992

INVENTOR(S) : Ernst Knorpp, et al.

It is certified that error appears in the above-identified patent and that said Letters Patent is hereby corrected as shown below:

Column 4, line 27: delete ", changes!" and insert --.--

Column 6, line 31: "spacc" should read as --space--

Column 8, line 39: "comparispn" should read as --comparison--

Column 9, line 48: "oontrolled" should read as --controlled--

Column 11, line 56: "reasoh" should read as --reason--

Column 14, line 16: delete "10"

Column 15, line 56: after "Heating" insert --Program--

Column 16, line 57: "temperaturc" should read as --temperature--

Column 16, line 58: "sct" should read as --set--

Column 17, line 5: after "time" insert -- ⊓⊓⊓⊓ --

Column 17, line 33: "plessed" should read as --pressed--

UNITED STATES PATENT AND TRADEMARK OFFICE
CERTIFICATE OF CORRECTION

PATENT NO. : 5,072,360
DATED : December 10, 1992
INVENTOR(S) : Ernst Knorpp, et al.

It is certified that error appears in the above-identified patent and that said Letters Patent is hereby corrected as shown below:

Column 19, line 53: "50°" should read as --850°--

Column 21, line 32: "heabing" should read as --heating--

Column 22, line 31: "1s" should read as --is--

Column 22, line 59: "thout" should read as --without--

Column 23, line 33, Claim 1: "program" should read as --programs--

Column 23, line 39, Claim 1: "seleted" should read as --selected--

Column 23, line 47, Claim 1: "peiods" should read as --periods--

Column 24, line 15, Claim 9: after "program" insert --is--

Column 24, line 19, Claim 10: "the" should read as --a--

Column 24, line 22, Claim 11: delete "the"

UNITED STATES PATENT AND TRADEMARK OFFICE
CERTIFICATE OF CORRECTION

PATENT NO. : 5,072,360
DATED : December 10, 1992
INVENTOR(S) : Ernst Knorpp, et al.

It is certified that error appears in the above-identified patent and that said Letters Patent is hereby corrected as shown below:

Column 24, line 22, Claim 11: "is" should read as --are--

Column 24, line 25, Claim 12: delete "the"

Column 24, line 46, Claim 18: "the" should read as --a--

Column 25, line 14, Claim 29: after "claim" delete --,--

Signed and Sealed this

Twenty-first Day of September, 1993

Attest:

BRUCE LEHMAN

*Attesting Officer*  *Commissioner of Patents and Trademarks*